United States Patent
Luciw et al.

[11] Patent Number: 6,004,799
[45] Date of Patent: Dec. 21, 1999

[54] RECOMBINANT LIVE FELINE IMMUNODEFICIENCY VIRUS AND PROVIRAL DNA VACCINES

[75] Inventors: Paul A. Luciw, Davis; Ellen E. Sparger, Dixon, both of Calif.

[73] Assignee: The Regents of the University of California, Oakland, Calif.

[21] Appl. No.: 08/811,828

[22] Filed: Mar. 5, 1997

Related U.S. Application Data

[63] Continuation-in-part of application No. 08/691,662, Aug. 2, 1996, abandoned, which is a continuation-in-part of application No. 08/611,321, Mar. 5, 1996, abandoned.

[51] Int. Cl.⁶ .............................. C12N 7/04; A61K 39/00; C12Q 1/70; C07H 21/02
[52] U.S. Cl. .................. 435/236; 424/192.1; 424/208.1; 435/5; 435/172.3; 536/23.1
[58] Field of Search ............................. 424/192.1, 208.1; 435/5, 172.3, 236; 536/23.1

[56] References Cited

U.S. PATENT DOCUMENTS

| | | |
|---|---|---|
| 5,017,487 | 5/1991 | Stunneberg et al. . |
| 5,152,982 | 10/1992 | Parkes et al. . |
| 5,275,813 | 1/1994 | Yamamoto et al. . |
| 5,413,927 | 5/1995 | Tompkins et al. . |
| 5,510,106 | 4/1996 | Yamamoto et al. . |
| 5,589,466 | 12/1996 | Felgner et al. . |

FOREIGN PATENT DOCUMENTS

| | | | | |
|---|---|---|---|---|
| WO 92/00987 | 1/1992 | WIPO | ............................. | C07H 15/12 |
| WO 94/17825 | 8/1994 | WIPO | ............................. | A61K 39/12 |
| WO 95/04546 | 2/1995 | WIPO | ............................. | A61K 39/21 |
| WO 95/16784 | 6/1995 | WIPO | ............................. | C12N 15/86 |

OTHER PUBLICATIONS

Benvenisty, N. et al., "Direct introduction of genes into rats and expression of the genes," *Proc. Natl. Acad. Sci. U.S.A.* 83:9551–9555 (1986).

Clements, J.E. et al., "Molecular biology of lentiviruses," *Sem. Virol.* 3:137–146 (1992).

Diehl, L.J. et al., "Longitudinal Assessment of Feline Immunodeficiency Virus Kinetics in Plasma by Use of a Quantitative Competitive Reverse Transcriptase PCR," *J. Virol.* 69(4):2328–2332 (1995).

Giavedoni, L.D. et al., "SIV$_{\Delta nef}$ expressing INF–γ is a more attenuated and efficacious vaccine than SIV$_{\Delta nef}$," 13th Ann. Symp. Nonhuman Primate Models for AIDS, Nov. 5–8, 1994, Monterey, CA, Abstract 24.

Ho, S.N. et al., "Site–directed mutagenesis by overlap extension using the polymerase chain reaction," *Gene* 7:51–59 (1989).

Hosie, M.J., "The Development of a Vaccine Against Feline Immunodeficiency Virus," *Br. vet. J.* 150:25–39 (1994).

Lawrence, C.E. et al., "Decreased mitogen responsiveness and elevated tumor necrosis factor production in cats shortly after feline immunodeficiency virus infection," *Vet. Immunol. Immunopath.* 35:51–59 (1992).

Letvin, N.L. et al., "Risks of handling HIV," *Nature* 349:573 (1991).

(List continued on next page.)

*Primary Examiner*—Jeffrey Stucker
*Assistant Examiner*—Hankyel T. Park
*Attorney, Agent, or Firm*—Townsend and Townsend and Crew LLP

[57] ABSTRACT

This invention discloses live-attenuated feline immunodeficiency virus (FIV), and recombinant vectors for producing them, useful as vaccines and therapeutic agents against FIV and diseases associated with virulent FIV infection. In the recombinant vectors and FIVs, one or more genes, or part of the gene(s), responsible for FIV pathogenesis have been completely or partially rendered nonfunctional, e.g., by full or partial deletion or mutagenesis. These anti-FIV vaccines may be given to susceptible hosts in the form of infectious virus or cloned DNA.

38 Claims, 7 Drawing Sheets

OTHER PUBLICATIONS

Luria, S. et al., "Expression of the type 1 human immunodeficiency virus Nef protein in T cells prevents antigen receptor–mediated inductionof interleukin 2 mRNA," *Proc. Natl. Acad. Sci. U.S.A.* 88:5326–5330 (1991).

Mayo, K.E. et al., "The Mouse Metallothionein–I Gene is Transcriptionally Regulated by Cadmium following Transfection into Human or Mouse Cells," *Cell* 29:99–108 (1982).

Miyazawa, T. et al., "The AP–1 binding site in the feline immunodeficiency virus long terminal repeat is not required for virus replication in feline T Lymphocytes," *J. Gen. Virol.* 74:1573–1580 (1993).

Montelaro, R.C. et al., "Vaccines against Retroviruses," *The Retroviridae* vol. 4, J.A. Levy, ed., Plenum Press, New York, pp. 605–656 (1995).

Nicolau, C. et al., "In vivo expression of rat insulin after intravenous administration of the liposome–entrapped gene for rat insulin I," *Proc. Natl. Acad. Sci. U.S.A.* 80:1068–1072 (1983).

Olmsted, R.A. et al., "Molecular cloning of feline immunodeficiency virus," *Proc. Natl. Acad. Sci. U.S.A.* 86:2448–2452 (1989).

Phillips, T.R. et al., "Comparison of Two Host Cell Range Variants of Feline Immunodeficiency Virus," *J. Virol.* 64(10):4605–4613 (1990).

Portis, J.L. et al., "Infectivity of Retroviral DNA In Vivo," *J. Acq. Immune Deficiency Syndromes* 5:1272–1277 (1992).

Shacklett, B.L. et al., "Analysis of the VIF Gene of Feline Immunodificiency Virus," *Virology* 204:860–867 (1994).

Seeger, C. et al., "The cloned genome of ground squirrel hepatitis virus is infectious in the animal," *Proc. Natl. Acad. Sci. U.S.A.* 81:5849–5852 (1984).

Sparger, E.E. et al., "Regulation of Gene Expression Directed by the Long Terminal Repeat of the Feline Immunodeficiency Virus," *Virology* 187:165–177 (1992).

Sparger, E.E. et al., "Infection of Cats with Molecularly Cloned and Biological Isolates of the Feline Immunodeficiency Virus," *Virology* 205:546–553 (1994).

Talbott, R.L. et al., "Nucleotide sequence and genomic organization of feline immunodeficiency virus," *Proc. Natl. Acad. Sci. U.S.A.* 86:5743–5747 (1989).

Thompson, F.J. et al., "Cis– and trans–regulation of feline immunodeficiency virus: identificationof functional binding sites in the long terminal repeat," *J. Gen. Virol.* 75:545–554 (1994).

Tomonaga, K. et al., "The Feline Immunodeficiency Virus ORF–A Gene Facilitates Efficient Virla Replication in Established T–Cell Lines and Peripheral Blood Lymphocytes," *J. Virol.* 67(10):5889–5895 (1993).

Ulmer, J.B. et al., "Heterologous Protection Against Influenza by Injection of DNA Encoding a Viral Protein," *Science* 259:1745–1749 (1993).

Wolff, J.A. et al., "Direct Gene Transfer into Mouse Muscle in Vivo," *Science* 247:1465–1468 (1990).

Wu, G.Y. et al., "Receptor–mediated Gene Delivery and Expression in Vivo," *J. Biol. Chem.* 263(29):14621–14624 (1988).

Yamamoto, J.K. et al., "Experimental Vaccine Protection Against Feline Immunodeficiency Virus," *AIDS Res. and Human Retroviruses* 7(11):911–922 (1991).

T. Yilma et al. Abstract from "Conference On Advances In AIDS Vaccine Development", 8th Annual Meeting of the National Cooperative Vaccine Development Groups for AIDS, Feb. 11–15, 1996.

RECOMBINANT LIVE FELINE IMMUNODEFICIENCY VIRUS AND PROVIRAL DNA VACCINES

This patent application is a continuation-in-part of U.S. patent application Ser. No. 08/691,662, filed on Aug. 2, 1996, now abandoned, which was a continuation-in-part of U.S. patent application Ser. No. 08/611,321, filed on Mar. 5, 1996, now abandoned.

This invention was made with Government support under Grant Nos. R29-AI34776 and RO1-AI28580 awarded by the National Institute of Health. The Government has certain rights to this invention.

FIELD OF THE INVENTION

This invention relates to the field of viral vaccines, particularly live attenuated recombinant feline immunodeficiency viruses (FIV) and proviral DNA that are especially useful against FIV and the acquired immunodeficiency disease caused by FIV.

BACKGROUND OF THE INVENTION

Feline immunodeficiency virus (FIV) is an exogenous retrovirus of the Lentivirus genus and is associated with a fatal acquired immunodeficiency syndrome (AIDS)-like disease in domestic cats. FIV is similar in genetic organization and virion morphology to other members of the genus lentivirinae, including: human immunodeficiency virus types 1 and 2 (HIV-1, HIV-2), simian immunodeficiency virus (SIV), visna-maedi virus (VMV), equine infectious anemia virus (EIAV), caprine arthritis-encephalitis virus (CAEV), and bovine immunodeficiency-like virus (BIV) {Clements, J. E., et al., *Seminars in Virology,* 3:137–146 (1992); and Shacklett, B. L., et al., *Virol.,* 204:860–867 (1994)}. Both HIV and FIV cause a fatal syndrome in their respective hosts. This syndrome is characterized by generalized lymphadenopathy and increased susceptibility to opportunistic infections.

Biological FIV-PPR and isolates of molecular clones of FIV-pF34 (the molecular proviral clone of the latter is termed pF34) are described in Talbott, R. L., et al., *PNAS (USA),* 86:5743–5747 (1989). The molecular clone FIV-pF34 infected Crandell feline kidney (CrFK) and G355-5 cell lines, but replicated less efficiently in feline peripheral blood leukocytes (Id.). In contrast, the PPR clone productively infected the primary feline peripheral blood leukocytes but not CrFK or G355-5 cells (Id.). The isolate of another molecular clone, FIV-pPPR (the molecular proviral clone is termed pPPR) was reported in Phillips, T. R., et al., *J. Vir.,* 64(10):4605–4613 (1990). The two viral isolates (pPPR and pF34) show more than 85% sequence homology {Sparger, E. E., et al., *Virol.,* 187:165–177 (1992)}.

Lentiviruses have complex genomes which encode structural proteins (e.g., Gag, Pol, and Env) as well as regulatory proteins (e.g., Tat, Rev) and accessory proteins (e.g., Vif, Nef, Vpr, Vpx, Vpu) (Id). FIV has been shown to encode a rev gene and a vif gene, but appears to lack genes corresponding to tat, nef, vpr, vpx, and vpu (Id).

Tomonaga, et al., reported that mutation of a short conserved region designated open reading frame A (ORF-A) in FIV clone TM-2 produced a virus that replicated with delayed kinetics in feline lymphoid cell lines and peripheral blood lymphocytes (PBL) {Tomanaga, K., et al., *J. Virol.,* 67:5889–5895 (1993)}. Shacklett, et al., supra, made three mutations in the vif gene of molecular clone FIV-pF34: (i) deletion of 223 bp from the central portion of the gene; (ii) site-directed mutation of a conserved N-terminal basic region; and (iii) site-directed mutation of a conserved C-terminal motif. FIV proviruses containing each of these mutations were tested for replication following transfection into two feline adherent cell types, CrFK and G355-5. All three vif mutants produced very little cell-free virus or viral protein in both cell types (Id.).

The long terminal repeat (LTR) of a retrovirus contains sequence elements that constitute a promoter for controlling viral gene expression in infected cells. The FIV LTR was found to contain an element (i.e., a potential AP-1 site) upstream from the TATA box which was required for responses to T-cell activation signals. In addition, transcription directed by the LTR responded to an inducer of intracellular cyclic-AMP (c-AMP) (i.e., forskolin). Mutagenesis studies revealed that a potential ATF site, also known as a c-AMP response element (CRE) is required for activation by either forskolin or dibutyryl c-AMP.

FIV LTR mutations affecting the first AP4 site, AP1 site, ATF site, or NF-KB site resulted in decreased basal promoter activity of LTR as measured in various cell lines in transient expression assays using plasmids containing the viral LTR linked to the bacterial chloramphenicol acetyltransferase gene {Sparger, E. E., et al., *Virol.,* 187:165–177 (1992)}. Miyazawa, T., et al., deleted sequences of 31 bp containing putative AP-1 and AP-4 binding sequences in the U3 region of FIV LTR {Miyazawa, T., et al., *J. Gen. Virol.,* 74:1573–1580 (1993)}. The mutated LTR was introduced into an infectious molecular clone of FIV and the replication rate and the cytopathogenic activity of the mutant were compared with those of the wild type in two feline CD4-positive T lymphoblastoid cell lines. Miyazawa, T., et al., found that the rate and activity of the mutant were almost the same as those of the wild type. Miyazawa, T., et al., concluded that the 31 bp fragment was important for achieving maximal expression of the FIV genome, but not required for the replication of FIV in feline T lymphocytes.

It has been long recognized that DNA of molecularly cloned DNA viruses can be highly infectious in vivo, but the infectious nature of retroviral DNA in vivo has not been generally appreciated. See, for example, the disclosures of U.S. Pat. Nos. 5,589,466 and 5,152,982. However, Myrick, K. V., et al., found that intact SIVmac could be isolated from peripheral blood lymphocytes of three of four *Macaca fascicularis* monkeys which were inoculated, intramuscularly, with SIVmac proviral DNA. Letvin, N. L., et al., *Nature,* 349:573 (1991). Infectious virus was also detected in the spleens of mice after injection with cloned chimeric murine retroviral DNA of FrCas$^E$. Portis, J. L., et al., *J. Acquired Immune Deficiency Syndrome,* 5:1272–1277 (1992). A plasmid containing an unpermuted genome of FB29, flanked by two LTRs, was infectious when injected as supercoiled DNA (without excision of the viral genome). Id.

Ulmer, J. B., et al., injected plasmid DNA encoding influenza A nucleoprotein into the quadriceps of BALB/c mice. This resulted in the generation of nucleoprotein-specific cytotoxic T-lymphocytes and protection from a subsequent challenge with a heterologous strain of influenza A virus, as measured by decreased viral lung titers, inhibition of mass loss, and increased survival. Ulmer, J. B., et al., *Sci.,* 259:1745–1749 (1993). RNA and DNA expression vectors containing genes for chloramphenicol acetyltransferase, luciferase, and β-galactosidase were separately injected into mouse skeletal muscle in vivo. Protein expression was readily detected in all cases, and no special delivery system was required for these effects. Wolff, J. A., et al., *Sci.,* 247:1465–1468 (1990).

The preparation of vaccines to protect feline hosts against FIV infection is discussed in U.S. Pat. Nos. 5,275,813 and 5,510,106 and in Hosie (1994) Br. Vet. J. 150:25–39.

SUMMARY OF THE INVENTION

One aspect of the present invention presents live attenuated FIVs and/or their proviral DNAs, preferably in the form of vaccine compositions, which are preferably infectious, but are attenuated in pathogenicity and not lethal to their hosts, though capable of eliciting and enhancing the host's immune response against unattenuated FIVs. These vaccines are useful for immunizing hosts against FIVs and against viruses related to FIVs and the diseases caused by them and are capable of both inhibiting initial infection in seronegative hosts and reducing infection (viremia) in seropositive hosts. The attenuated FIVs preferably lack one or more genes and/or genetic elements of FIV which are responsible for pathogenicity, particularly binding sites within the LTR for enhancer/promoter proteins, such as those for AP-1 and ATF. Alternatively, those genes and/or genetic elements are partially or fully nonfunctional in the attenuated FIVs. The recombinant vectors for producing the live attenuated FIVs and proviral DNAs are also presented.

Another aspect of the invention presents live attenuated viruses and proviral DNAs of the above which additionally contain one or more exogenous genes encoding one or more cytokines, lymphokines, and/or toxins.

Another aspect of the invention presents vaccination and therapeutic methods comprising administering to a host the above live attenuated FIVs and/or proviral DNAs.

Another aspect of the invention presents pharmaceutical compositions, useful as vaccines and therapeutics, which contain the above live attenuated FIVs and/or proviral DNAs.

Another aspect of the invention presents methods for producing the above live attenuated FIVs and/or proviral DNAs.

Another aspect of the invention presents methods for immunizing or treating a host against FIV infection which achieves protective immunity after a single dose of a non-naturally occurring attenuated FIV and/or a non-nationally occurring FIV vector. By "protective immunity," it is meant that the host is protected against infection by a natural FIV, where the natural FIV is unable to mount a deleterious infection, i.e. the detectable viral load of the natural virus is absent or sufficiently low so that the heath of the host is not significantly compromised.

Another aspect of the invention presents methods for treating seropositive cats, previously infected with wild type FIV, by administering a non-naturally occurring attenuated FIV or a non-naturally occurring FIV vector, where such treatment can reduce the viral load of the wild type FIV.

Another aspect of the invention presents vaccine compositions comprising self-replicating proviral DNA constructs comprising substantially the entire genome of a lentivirus, such as FIV, HIV, SIV, equine infectious anaemia virus, visna virus, caprine arthritis encephalitis virus, and bovine immunodeficiency virus. The lentivirus genome has at least one deletion, substitution, reversion, or other mutation, which is located in a region of the genome responsible for transcription initiation or multiplication. Preferably, the DNA construct comprises a circular DNA plasmid having replication and transcription regions suitable for replication in a prokaryotic host, preferably *E. coli*, or another common cloning host. The deletions in the lentivirus genome are preferably in the LTR, more preferably being in transcriptional control elements, such as AP1, AP4, ATF, NF-κB, C/EBP, and LBP1. Hosts may be treated by direct administration of the proviral DNA constructs, preferably intramuscularly. Such administration of the proviral DNA constructs results in the production and release of non-natural lentivirus particles which are infectious at a low level and replication competent, and which inhibit subsequent infections by wild type virus.

BRIEF DESCRIPTION OF THE DRAWINGS

FIG. 1B. FIV-pPPRΔVIF; and starting from FIG. 1C. FIV-pPPR, for generating: FIG. 1D. FIV-pPPRΔAP-1, FIV-pPPRΔATF and FIV-pPPRΔAP-1/ATF. These are designated Type 1 mutants.

FIG. 3C. FIV-pPPR-pSVΔVif.

DESCRIPTION OF THE PREFERRED EMBODIMENT

Figure 1A:
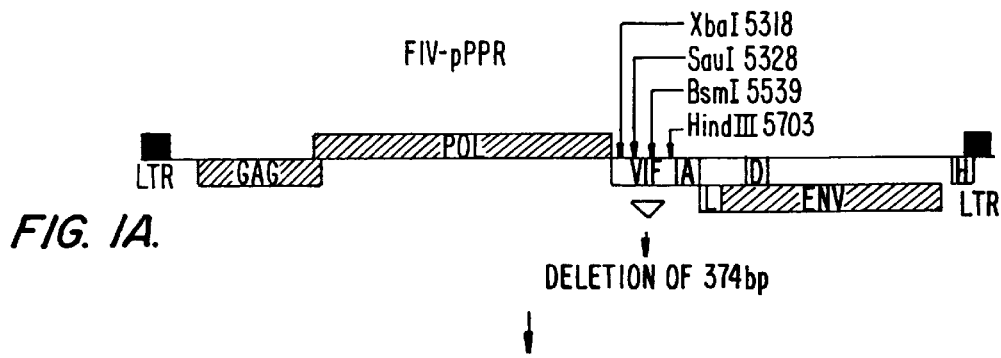
FIGS. 1A to 1D schematically present the strategy, starting from FIG. 1A. FIV-pPPR, for generating.
Figure 1B:
Figure 1C:
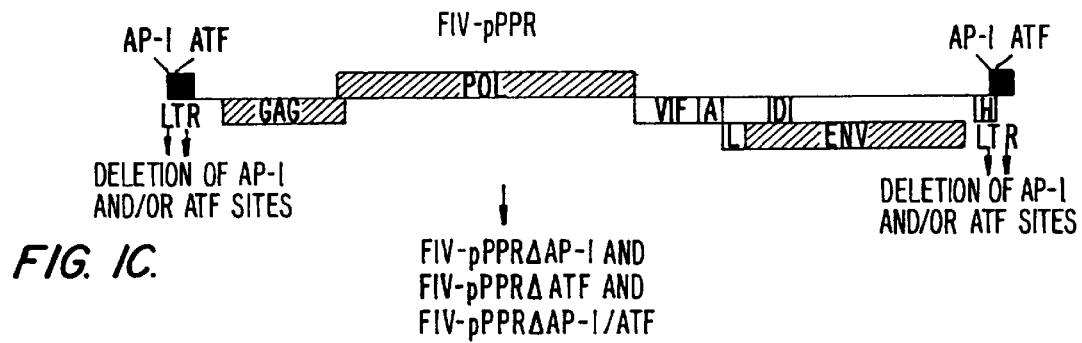
Figure 1D:
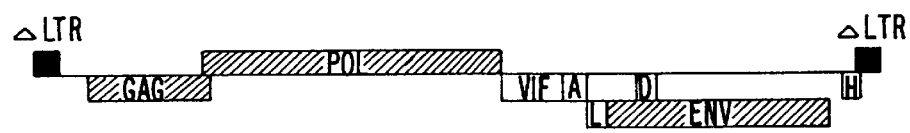

The following is a list of the abbreviations and their definitions as used in this application:

AIDS—acquired immunodeficiency syndrome
BIV—bovine immunodeficiency virus
bp—base pair(s)
c-AMP—cyclic-AMP
CAEV—caprine arthritis-encephalitis virus
CRE—c-AMP response element
CrFK—Crandell feline kidney
DNA—deoxyribonucleic acid; "DNAs" denotes the plural form
EIAV—equine infectious anemia virus
FIV—Feline immunodeficiency virus; "FIVS" denotes the plural form
HIV—human immunodeficiency virus
LTR—long terminal repeat
ORF-A—open reading frame A
PBL—peripheral blood lymphocytes
PBMC—peripheral blood mononuclear cells
PCR—polymerase chain reaction
SIV—simian immunodeficiency virus
$TCID_{50}$—50% tissue culture infective dose
VMV—visna-maedi virus
WT—wild type The present invention presents vaccine compositions comprising live attenuated FIVs and vectors which are attenuated in pathogenicity and not lethal to the host but yet are still capable of evoking a fully or partially protective immune response in an immunized host. These vaccines are shown to be effective against FIV and its related pathogens, and diseases associated with virulent infection by FIV or its related pathogens. Preferably, the attenuated FIVs and vectors remain at very low viral loads. More preferably, they do not persist in their vaccinated host. Preferably, the attenuated FIVs and vectors prevent initial infection of the host by unattenuated (wild type) FIV, or limit dissemination and establishment of the unattenuated FIV once it has infected the host. More preferably, the attenuated FIVs and vectors are capable of eliciting and enhancing the host's immune response against the unattenuated FIVs. Preferably, both the humoral and cellular immune responses are enhanced. The attenuated FIVs and vectors are preferably replication-competent and infectious. These live attenuated FIVs and vectors are derived from or related to members of their pathogenic species but they do not contain one or more genes and/or genetic elements of FIVs which are responsible for their pathogenicity, or these genes and/or genetic elements are partially or fully nonfunctional in the attenuated FIVs and vectors. More preferably, the live attenuated FIVs and vectors are recombinantly derived from naturally occurring unattenuated or attenuated FIVs, e.g. by recombinant method, by modifying the genes and/or genetic elements responsible for pathogenicity such that they are absent, rendered non-functional or partially functional.

Included in the definition of "vectors" are the substantially intact genomes of the attenuated FIVs (intact except for the deletions discussed below), and their complementary nucleotide sequences, such as deoxyribonucleotide and ribonucleotide acid sequences (DNA and RNA, respectively). In the present invention of attenuated RNA viruses, the vectors may include the viral RNA genome, but proviral DNA and cDNA of the viral RNA are preferred. Though linearized DNA may be used, the DNA is preferably in the form of plasmid DNA, particularly circular plasmid DNA which is less likely to become integrated into the host genome. In the present invention, the more preferred vaccine vector is proviral DNA integrated into a circular bacterial plasmid. The most preferred vaccine vector is a live infectious proviral DNA integrated into a circular bacterial plasmid or construct.

The present invention also presents methods for producing these live attenuated FIVs and recombinant vectors. The recombinant vectors are preferably produced by mutagenizing or deleting the genes responsible for pathogenicity from a FIV.

In this application, the host includes any animal that is susceptible to infection by or harboring FIV. For the sake of convenience, in the following discussion, cats are used as examples of hosts and animal models, and are not to be construed as limiting the choice of hosts.

"Attenuation" as used herein is defined as reduced pathogenesis, e.g. reduced replication capacity or viral load of the attenuated FIV, as compared with wild type biological FIV, is synonymous with attenuation. The live attenuated FIVs and vectors are more immunogenic and offer more durable and broader protection than other types of vaccines because they best mimic infection with the (unattenuated) FIVs but do not retain the capacity to cause a full-blown disease. Therefore, they are more effective than vaccines based on inactivated whole FIVs, viral subunits, or live heterologous viral or bacterial vectors.

By "vaccine composition," it is meant that the live attenuated FIVs, proviral DNA, and/or vectors are provided in a sterile form (substantially free from infectious and injurious substances other than the immunogenic components) suitable for administration to the intended host, usually a cat, by any of the administrative routes described below. Usually, the viral and/or nucleic acid components of the vaccine compositions will be highly purified, usually with a purity of at least 80%, preferably at least 90%, more preferably at least 95%, and in some cases being as high as 99%, of total nucleic acids by weight. The viral and/or nucleic acid components may, of course, be combined with suitable carriers, adjuvants, liposomes, or the like, as described below. Preferred amounts, dosages, and forms of the FIVs, proviral DNA, and/or vectors are also described below.

The vaccine compositions will be provided in conventional sterile packages for vaccines, e.g. sterile ampoules with a septum for needle-injectable solutions and suspensions, blister packs for powders, and the like.

An example of a gene or genetic element that is responsible for pathogenesis, but which is absent, or fully or partially nonfunctional in the attenuated live FIVs and recombinant vectors is a regulatory or accessory gene. Examples of these genes are those which control viral load in the host. Preferably, these are nonessential genes, i.e. genes which can be deleted without completely abrogating the ability of FIV to replicate. Examples of such genes are: vif, rev, OrfA/2, LTR elements, env, pol, and gag. Further, though the env, gag, or pol genes are preferably not completely deleted, each can be mutated such that cell tropism, replication efficiency, and/or immunologic properties of the resulting virus are modified. More preferably, the genes and genetic elements are not required for productive infection but influence virus load, latency and/or reactivation, e.g., vif, rev, OrfA/2, LTR elements, etc.

In the preferred embodiment, the attenuation is a result of at least one mutation resulting in transcriptional debility of the viral pathogen. Preferably, the mutations include those in the LTR which inhibit binding of enhancer/promoter proteins, such as AP-1, AP-4, C/EBP, and ATF, particularly AP-1 and ATF. More preferably, the virus and vectors are double or triple mutants, e.g. with LTR and vif mutations or deletions to render them non-functional, or with additional mutations or deletions in other genes described above. The clone may be further recombinantly constructed to be driven by a SV40pr/RU5 promoter or other promoters which promote initiation of expression of the proviral DNA. The recombinant vectors or viruses may have other heterologous viral promoters, e.g. CMV immediate early promoter or other cellular promoter. Examples of promoters are metallothionein promoter, inducible by heavy metals {Mayo, K. E., et al., *Cell,* 29:99–108 (1982)}, hormone inducible promoter, and promoters which respond to cellular trans activators. Other promoters known for viral systems may also be used. These promoters may replace the FIV promoter using methods known in the art. When the recombinant viruses and vectors are driven by an inducible promoter, then the inducers are preferably present in the pharmaceutical composition to be administered to the cat. The inducible promoter can be selected such that their inducers are not endogenously abundant in the host, thus the production of the virus will become less over time in the host and enable more effective elimination of the viral vector by the host, over time. For example, if the promoter is steroid inducible, steroid is preferably present in the pharmaceutical composition to activate the production of the recombinant viruses in the cat. As initially administered, with the presence of the high level of steroid in the composition, the viruses will be very active. Over time, the initial administered steroid will dissipate and viral load will decrease though still activated by a low level of endogenous steroids in the host but the low viral load will eventually allow for elimination of the virus from the host system by anti-viral immune responses.

Another aspect of the invention presents the above attenuated FIV viruses and vectors which additionally contain one or more exogenous genes encoding one or more cytokines, lymphokines, and/or toxins. Examples of the cytokines, lymphokines, and toxins are: Interferon-α ("IFN-α"), IFN-β, IFN-γ, Interleukin-2 (I"L-2"), IL-12, cytokines which influence anti-viral mucosal immunity, cytokines which regulates secretory antibody levels, SI subunits of B. pertussis, and other immunostimulatory products from bacterial or other organisms. Due to the anti-viral activity of the cytokine or lymphokine, and the proximity of the toxin or immunostimulatory agent, it is envisioned that they will further attenuate the viruses and preferably eventually kill the viruses so they do not persist in the host. These attenuated vectors and viruses can be constructed and produced using methods known in the art, such as the methods disclosed in: Abstract 24 from "13th Annual Symposium on Nonhuman Primate Models for AIDS", hosted by the California Regional Primate Research Center, Nov. 5–8, 1995, Monterey, Calif.; Abstract, "Expression of Interferon-γ by Simian Immunodeficiency Virus Increases Attenuation and Vaccine Efficacy for Rhesus Macaques" by Yilma, T. et al., Conference on Advances in AIDS Vaccine Development, Eighth Ann. Mtg. Nat'l Cooperative Vaccine Development Groups for AIDS, Feb. 11–15, 1996; Poster 78 from "Conference on Advances in AIDS Vaccine Development: 1994, 7th Ann. Mtg. of the Nat'l Cooperative Vaccine Development Groups for AIDS", Div. of AIDS, Nat'l. Inst. of Allergy and Infectious Diseases, Reston, Va. (1994); and Abstract P25-9 from "Scientific Programs and Abstracts", American Society for Virology, 13th Ann. Mtg., Madison, Wis. (1994).

The viruses and vectors of the present invention may be constructed from any FIV strains or clones, the FIV-pPPR is used here merely as an example and is not to be deemed limiting of the possible strains or clones. Thus, for example, the constructs described in the "EXAMPLES" section below may also be similarly constructed from other FIV clones, such as FIV-Petaluma and FIV-pF34. Further, besides the wild type vectors or viruses, and those that are readily available or have been sequenced, starting materials of the present invention may also be recombinant or attenuated vectors or viruses, preferably those with reduced pathogenicity. The selection of the starting material, the deletion or mutagenization of the genes or genetic elements, the construction of vectors, the production, propagation, and purification of live attenuated FIVs and vectors, can be achieved based on the present disclosure and using methods known in the art such as described in Sambrook, et al., *Molecular Cloning: A Laboratory Manual*, (Cold Spring Harbor Laboratory Press, 2d ed., 1989) and Ausubel, F. M., et al., *Current Protocols in Molecular Biology*, Greene Publishing Associates, New York, (1993); the references in this application, such as Yamamoto, J. K., et al., *AIDS Res. and Hum. Retrovir.*, 7(11):911–922 (1991) and Sparger, E. E., et al., *Virol.*, 205:546–553 (1994), and the "EXAMPLES" section below.

Generally, one or more of the genes and/or genetic elements are modified. Two or three mutated genes are preferred, e.g. from the following selections.

In the case of the LTR, it is undesirable to completely delete or render non-functional the LTR or its U3 region. The LTR is preferably modified to reduce transcription initiation or multiplication of the virus or viral RNA. Optionally, but not necessarily, both the 5' and 3' LTR are mutated to avoid reversion. A portion of or all of the enhancer region of the LTR may be removed. Generally, at least one base will be involved, more usually at least two bases, preferably at least about 5 bases, and more preferably between 4 to 5 bases, and usually not more than 20 bases may be modified. Thus, deletions of up to 20 bases are possible. Preferably, viral transcription sites, such as NF-κB, are modified. The other preferred sites are AP-1, AP-4, and ATF sites, optionally of both the 3' and 5' LTR. More preferably, deletions are made in more than one of the sites, for example, at both the AP-1 and ATF sites. Double or triple mutations, especially deletions, are preferred. The modification results in diminution of the transcriptional activity resulting from the LTR, while substantially diminishing (but preferably not eliminating) the replication capability of the virus, as well as its pathogenicity.

Env, gag, or pol genes are preferably not completely deleted and neither are frameshift mutations desired. Each of these genes can be mutated such that cell tropism, replication efficiency, and/or immunologic properties of the resulting virus are modified. Thus, in the case of these genes, generally, at least 3 bases (i.e., one amino acid) may be modified, more usually at least 6 bases (i.e., two amino acids), and preferably at least about 21 bases (i.e., an immunologic epitope or functional domain).

In another example, one or more of the following: rev, OrfA/2, and vif genes can be rendered completely non-functional using methods known in the art. Examples of such methods are completely deleting the genes; or a frameshift mutation, such as caused by the insertion or deletion of a base. If the genes are not completely deleted or rendered non-functional by frameshift, as many of the bases may be modified to adversely affect the normal gene function or expression. In the case of the vif gene, generally, at least 100 bases will be modified, more usually at least 150 bases, preferably at least about 200 bases, and more preferably 300 or more bases, and usually not more than 600 bases. In the preferred embodiment, about 374 bases are deleted or modified, from about base pairs 5318 to 5706 of the vif gene. In the more preferred embodiment, 374 bases are deleted or modified, from base pairs 5318 to 5706 of the vif gene. For example, in the case of the rev gene, generally, at least 30 bases will be modified, more usually at least 50 bases, preferably at least about 100 bases, and more preferably 150 or more bases, and usually not more than 300 bases. The OrfA/2 gene may be analogously modified.

Thus, as shown above, in the above or other FIV genes or genetic elements to be modified, the modification preferably results in diminution of the transcriptional activity of the gene or genetic element, or production of non-functioning or less than optimally functioning gene products, which diminish the replication capability of the virus, as well as its pathogenicity. The modification to the viral DNA may involve a deletion, substitution, inversion, insertion, etc. Preferably, the modifications provide an extremely low, and more preferably, no possibility of reversion to wild type. In the case of the LTR, any other LTR in the construct is preferably changed to lessen or avoid complementarity by such other LTR to restore wild type transcriptional activity by recombination.

Examples of preferred attenuated viruses and vectors are: (1) recombinant FIV with about 374 bases deleted from about base pairs 5318 to 5706 of its vif gene; and the same recombinant FIV driven by an SV40pr/RU5 hybrid promoter; (2) recombinant FIV with about 4 to 5 nucleotides deleted from the AP-1 and/or ATF sites in the 3' and 5' LTR, and more preferably in the U3 region of the 3' LTR; and the same recombinant FIV driven by an SV40pr/RU5 hybrid promoter; (3) recombinant FIV with about 374 bases deleted from about base pairs 5318 to 5706 of its vif gene, and with about 4 to 5 nucleotides deleted from the AP-1 and/or ATF sites in the 3' and 5' LTR (more preferably in the U3 region of the 3' LTR); (4) the recombinant FIV of (3) driven by an SV40pr/RU5 hybrid promoter; (5) recombinant FIV with its vif gene, AP-1 and/or ATF sites in the 3' and 5' LTR deleted; and the same recombinant FIV driven by an SV40pr/RU5 hybrid promoter.

Deletion can be conveniently introduced where a restriction endonuclease site is present. This may involve insertion of the viral DNA into a convenient vector for amplification in a suitable host and purification, followed by molecular manipulation of the virus in the desired region. Preferably, the restriction endonuclease site for the genetic manipulation is unique to the desired gene or genetic element, although partial digestion can be employed. A deletion may then be introduced by treatment with a double-stranded specific exonuclease.

Other mechanisms known in the art may be used for modifying the genes or genetic elements. For example, primer mutagenesis by polymerase chain reaction can provide for alteration at a particular site in the gene or genetic element and loss of the gene or genetic element upstream from that site. In vitro mutagenesis can provide for deletions, insertions, or mutations. Site-directed mutagenesis may also be used, e.g., as described in Ho, S. N., et al., *Gene,* 77:51–59 (1989); Ausubel, F. M., et al., *Current Protocols in Molecular Biology,* Greene Publishing Associates, New York (1993); and the "EXAMPLES" section, below. Transposons may also provide for deletions.

As an example, once the appropriate vector has been obtained and cloned, the plasmid containing the viral DNA may be used as a provirus for either transfection of tissue culture host cells and passaging or introduction into an animal via inoculation. From transfected cells showing virus production, which can be determined by any convenient assay, the viruses may be recovered by any convenient procedure. Alternatively, the virus may be harvested and used for infection of a host and the host bled to produce additional virus.

The vectors and live attenuated FIVs of the present invention can then be tested for their safety, vaccinating and therapeutic abilities, for example in the appropriate animal models or target animals, using techniques known in the art. Such techniques may be based on the disclosure in this application, and techniques known in the art, such as described in Yamamoto, J. K., et al., *AIDS Res. and Hum. Retrovir.,* 7(11) :911–922 (1991); Sparger, E. E., et al., *Virol.,* 205:546–553 (1994); Montelaro, R. C., et al., Vaccines against retroviruses, In: *The Retroviridae,* 4:605–656, Ed. J. A. Levy, Plenum Press, New York, (1995); and Powell, M. F., et al., *Vaccine Design-The Subunit and Adjuvant Approach,* Plenum Press, New York (1995). The vaccination and challenge protocols may be similarly formulated. For example, Yamamoto, J. K., et al., supra, describes clinical evaluations of vaccinated cats in which the cats were monitored daily for overt clinical symptoms. Weekly physical examinations, including weight measurements, were performed by a veterinarian. Laboratory examinations included routine hematology, FIV serology, and virus isolation (by Southern blot and PCR) done every 2–3 weeks during the early stages of infection. Evaluation of FIV humoral responses was performed by enzyme-linked immnunosorbent assay (ELISA), immunoblot and neutralization assays. T-cell proliferation and IL-2 assays were also conducted. Further, the safety of the vaccine is also assayed. Safety tests may involve monitoring cats for any adverse response such as fever within 24 hours of inoculation, e.g. resulting from endotoxin contamination of plasmid DNA preparations.

Essentially, the same assay systems for measuring virus load and anti-viral immune responses will be used to monitor the vaccinated cats, after challenge with pathogenic virus. In addition, PCR amplification will be used to distinguish mutant from wild type virus or genes in samples from challenged cats. The live attenuated virus would be considered efficacious as a vaccine if the assays do not produce detectable challenge virus, produces low viral load in vivo (compared with animal infected with virulent virus), produces lower challenge virus load, induction of antiviral antibodies or cellular response, and/or elimination, prevention, or reduction of FIV disease in the vaccinated cats. The vectors, live attenuated FIVs, and protocols are then retained or modified according to the results. Preferably, the vaccine is safe in very young recipients and immunocompromised animals (e.g., animals which are malnourished and whose immune system may be weakened by other infectious agents), is capable of inducing broad immunity necessary to protect's against from diverse viral strains, protect challenge via cell-associated virus or across mucosal membranes. The dosage to be administered is determined based on the tests on the animal model. For example, depending on the efficacy of the dosage in protecting the vaccinated cats against viral challenge, it may be increased or diluted.

By way of example, procedures for characterizing or analyzing the safety and efficacy of FIV plasmid vaccines, and determining the vaccination protocol (including dosage) are similar to those used to evaluate the attenuated virus, described above. One skilled in the art would be able to determine the appropriate vaccination methods based on the teaching of the present invention and methods known in the art.

In the case of live attenuated viruses as vaccines, they may be delivered intramuscularly, intradermally, intravenously, intraperitoneally, subcutaneously, nasal, and orally. Preferably, intramuscular injections, oral and nasal ingestion of the live attenuated viruses will be the primary route for vaccination or therapeutic administration, though intramuscular or subcutaneous administration may also be used.

The recombinant vectors of the present invention, such as plasmid proviral DNA (suitably purified and in a sterile form as defined above), can be directly injected into a cat using methods known in the art, e.g. by microinjection or particle bombardment such as by gene gun {see e.g., Yang, N. et al., *Gene Therapeutics,* J. A. Wolff, ed., Birkhauser, Massachusetts, USA (1994)}. Preferably, the recombinant vectors are solubilized in physiologically acceptable carriers. Other methods known in the art may also be used. For example, direct in vivo gene transfer may be also be achieved with formulations of DNA encapsulated in liposomes, DNA entrapped in proteoliposomes containing viral envelope receptor proteins {e.g., using the method disclosed in Nicolau, C., et al., *PNAS (USA),* 80:1068 (1983), hereby incorporated by reference in its entirety}, calcium phosphate-coprecipitated DNA {e.g., using the method disclosed in Benvenisty, N., et al., *PNAS (USA),* 83:9551 (1986), hereby incorporated by reference in its entirety}, and DNA coupled to a polylysine-glycoprotein carrier complex {e.g., using the method disclosed in Wu, G.

Y., *J. Biol. Chem.*, 263:14621 (1988), hereby incorporated by reference in its entirety}. In vivo infection with cloned viral DNA sequences after direct intrahepatic injection with or without formation of calcium phosphate coprecipitated DNA may also be used {e.g., using the method disclosed in Seeger, C., et al., *PNAS (USA)*, 81:5849 (1984), hereby incorporated by reference in its entirety}. Injection of pure RNA or DNA directly into the cats, such as into their muscle cells, may also be used {e.g., using the method disclosed in Wolff, J. A., et al., *Sci.*, 247:1465–1468 (1990), hereby incorporated by reference in its entirety}. Thus, the pure RNA or DNA may be delivered intramuscularly, intradermally, intravenously, intraperitoneally, subcutaneously, nasal, pulmonary, and orally. The preferred route of administration is by injection of DNA intramuscularly and intradermally. For intraperitoneal and intravenous delivery, lipid is preferably used, as described above, to enhance delivery. Methods such as liposomes may also be used to achieve inoculation of FIV plasmid through mucosal membranes {Powell, M. F., et al., *Vaccine Design-The Subunit and Adjuvant Approach*, Plenum Press, New York (1995)}.

The concentration of the dosage is preferably sufficient to provide an effective immune response. The dosage of the recombinant vectors and viruses administered will depend upon the properties of the formulation employed, e.g., its in vivo plasma half-life, the concentration of the recombinant vectors and viruses in the formulation, the administration route, the site and rate of dosage, the clinical tolerance of the cat involved, the pathological condition afflicting the cat, the age of the cat, and the like, as is well within the skill of one skilled in the art. Different dosages may be utilized in a series of inoculations; the practitioner may administer an initial inoculation and then boost with relatively smaller doses of the recombinant vectors or viruses or recombinant viral subunits or other boosters further described below.

The vaccine or therapeutic composition (herein collectively called "vaccine compositions"), will include a sufficient amount of either the live attenuated virus or the live attenuated proviral DNA, or combination thereof to provide an immune response. The composition may also contain different types of live attenuated viruses and/or vectors. Further, the composition may contain attenuated viruses and/or vectors from different strains of FIV to provide a broad based protection. Alternatively, the different live attenuated viruses and/or vectors may be contained in different compositions, to be separately or simultaneously administered. Each composition can be stored in individual vials. The vials may be packaged as kits for a broad based inoculation. The kits may further contain one or more other vials containing compositions for boosters, the compositions for boosters are further described below.

The vaccine compositions comprising live attenuated viruses and proviral DNA can be prepared for administration by mixing them at the desired degree of purity with physiologically acceptable carriers, i.e. carriers which are nontoxic to recipients at the dosages and concentrations employed, such as phosphate buffered saline solution, sterile water, with or without adjuvant.

In the preferred embodiment, the cats are preferably inoculated once with the proviral DNA plasmid or live attenuated virus. The preferred dose range is between about 30 $\mu$g to about 1 mg DNA, and more preferably between about 50 $\mu$g to 500 $\mu$g. The preferred dose range for live attenuated virus is between about $10^4$ to about $5\times10^6$, usually $5\times10^5$, focus-forming units. In the case of proviral DNA plasmid, lower doses may be used as plasmid expression and inoculation are optimized. Dosages may differ for adults in contrast to newborn kittens. The inoculation is preferably followed by boosters which could include whole killed FIV particles, recombinant FIV subunits, and/or heterologous vectors (bacterial or viral) such as pox virus, adenovirus, salmonella, and mycobacteria {Montelaro, R. C., et al., Vaccines against retroviruses, In: *The Retroviridae,* 4:605–656, Ed. J. A. Levy, Plenum Press, New York (1995)}.

The recombinant vectors and viruses may also be used to vaccinate animals which may or may not be at risk of exposure to FIV, and additionally, the vaccines are desirably administered to seropositive individuals and to animals which have been previously exposed to FIV. The vaccine may also be administered as therapeutics to animals suffering from diseases, such as immunodeficiency, caused by FIV.

The examples in this application are presented to illustrate some aspects of the invention, and are not to be construed as limiting the scope of the invention.

EXAMPLES

Example 1

Construction and Characterization of a VIF Deletion Mutant of FIV-pPPR (FIV-pPPRΔvif)

A. Construction of FIV-pPPRΔvif

The vif open reading frame is a conserved gene among the primate and most of the non-primate lentiviruses. An intact vif sequence has been found essential for efficient virus replication in primary PBMC and macrophages in the lentivirus systems tested so far.

In this Example, a region of 374 bases (bp 5318 to bp 5706) was deleted within the vif gene of the wild type (WT) molecular clone FIV-pPPR. The WT molecular clone was obtained from Dr. John Elder of the Scripps Research Institute, La Jolla, Calif., USA. The genome of FIV-pPPR is described in Phillips, T. R., et al., *J. Vir.,* 64(10):4605–4613 (1990), and the nucleotide and amino acid sequences are deposited with the GenBank with Accession Nos. M36968 and M25729, respectively. The locations of the genes described in these Examples are found in Phillips, T. R., et al., supra, and Talbott, R. L., et al., *PNAS* (*USA*), 86:5743–5747 (1989).

The construction is as follows. First, an approximately 4.7 kb subgenomic fragment containing a portion of the pol gene and the entire vif, orf-2, and env genes was digested from the FIV-pPPR provirus (cloned in the pUC19 vector) using EcoR5 (bp 4219) and Nde1 (bp 8900) sites within the provirus and cloned into the plasmid pSP72 (Promega Biotech, Madison, Wis., USA) to yield the construct PPR-R5N. Next, the plasmid PPR-R5N was digested with restriction enzymes Sau1 (bp 5328) and Hind3 (bp 5706) (in the vif gene) which deleted an approximately 374 bp internal fragment of vif. The digested PPR-R5N was gel purified away from the deleted 374 bp fragment, treated with the Klenow enzyme and religated to create a PPR-R5N construct with a deleted vif gene. Dideoxynucleotide sequencing of the vif-deleted PPR-R5N construct confirmed a 374 deletion within vif with loss of 2 bp from the Sau1 and 1 bp from the Hind3 site which produced an in-frame deletion. The EcoR5-Nde1 fragment containing the deleted vif was cloned from PPR-R5N back into the FIV-pPPR provirus to yield FIV-pPPRΔvif (FIG. 1). Dideoxynucleotide sequencing confirmed the presence of the 374 bp vif deletion in the FIV-pPPRΔvif construct. The cloning of the EcoR5-Nde1 fragment containing the deleted vif into pSV-pPPR WT to generate FIV-pPPR-pSVΔvif (FIG. 3) can be similarly made.

B. Characterization of FIV-pPPRΔvif.

Figure 7:
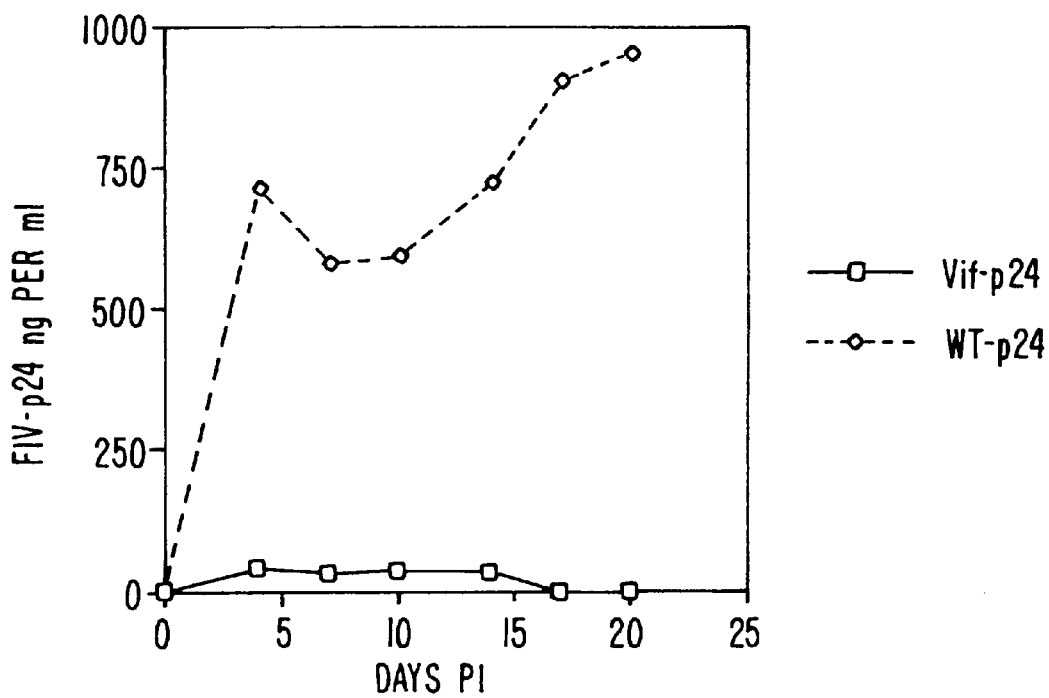
FIG. 7 graphically presents the replication of FIV-pPPRΔvif mutants in feline PBL.
Figure 8:
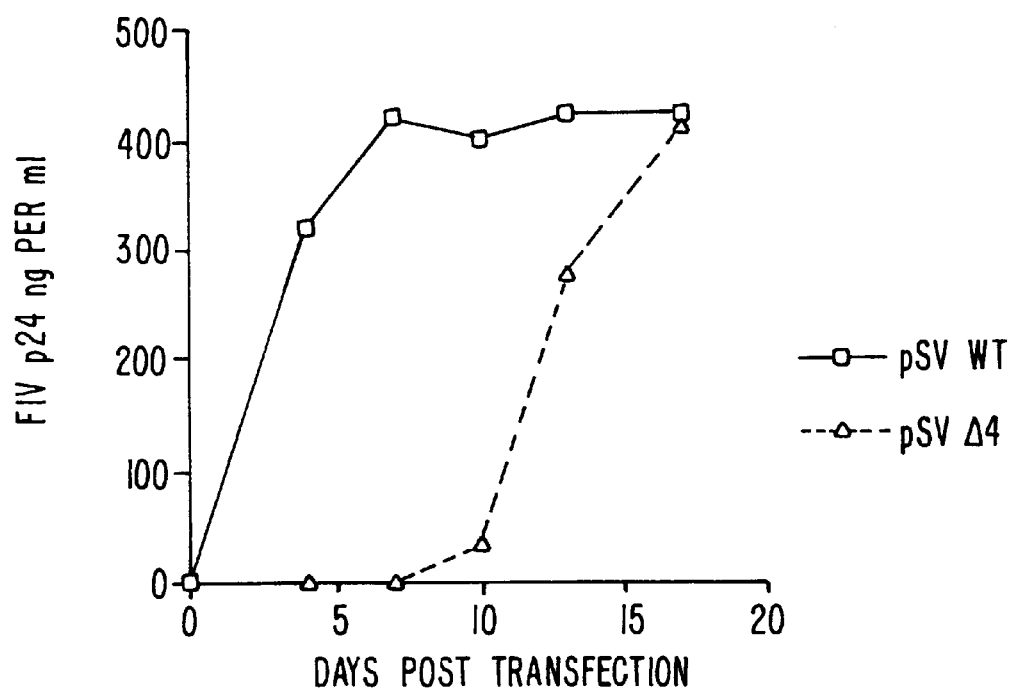
FIG. 8 graphically presents the replication of FIV pSVΔ4 mutants in PBMC.

For assessment of replication, CrFK cells were transfected with 10 μg of either FIV-pPPRΔvif or WT FIV-pPPR by electroporation and then cocultivated with primary feline PBMC on day 2 followed by isolation of the PBMC from CrFK cells on day 3. Supernatants from cocultivated PBMC were followed for FIV p24 by an antigen capture ELISA for up to 20 days post infection or cocultivation. Replication of FIV-pPPRΔvif in feline PBMC was found to be severely restricted when compared to WT FIV-pPPR in multiple experiments (FIG. 7). Expression of viral proteins (FIV p24 and envelope glycoprotein) in CrFK cells transfected with FIV-pPPRΔvif was confirmed by an immunocytochemical assay using antibodies. Experiments characterizing the replication of this mutant in feline lymphoid cell lines and macrophages are ongoing. As the molecularly cloned WT FIV-pPPR has been found to effectively induce a persistent viremia in experimentally inoculated cats, the vif deletion mutant of FIV-pPPR should provide a tool for evaluating the role of vif in FIV replication in vivo. The provirus designated FIV pPPR-pSVΔvif (FIG. 3) will be used for cat inoculation.

Example 2

Replication of Feline Immunodeficiency Virus LTR Mutant Viruses in Primary Feline Lymphocytes and Macrophages, Characterizations, and Use in Inoculating Cats Introduction AP-1 and ATF response elements within the U3 region of the feline immunodeficiency virus (FIV) long terminal repeat (LTR) are thought to serve as targets of cellular activation pathways and may provide sites for regulation of virus replication. The roles for the AP-1 and ATF sites in virus replication were assessed using LTR mutants constructed from the infectious molecular clone, FIV-pPPR. Type 1 LTR mutants consisting of AP-1 and/or ATF deletions (4 to 5 nucleotides) in the 3' and 5' LTR were transfected into CrFK cells, which were co-cultivated 24 hours later with primary feline peripheral blood mononuclear cells (PBMC). Deletion of the AP-1 element resulted in minimal reduction of replication, whereas deletion of the ATF site produced a moderate reduction of virus replication in feline PBMC compared with transfection of wild type (WT) FIV-pPPR. Virus production was significantly reduced in feline PBMC post transfection with Type 1 mutants containing deletion of both AP-1 and ATF sites.

Type 2 mutant proviruses constructed by replacement of the 5' LTR in WT with a SV40pr/RU5 hybrid promoter (pSVWT) and deletions of the AP-1 and/or ATF sites in the 3' LTR, were used to generate LTR mutant virus stocks. A moderate reduction of virus production was observed in feline PBMC post infection with Type 2 mutants containing deletions of the ATF site when compared with pSVWT. A greater reduction in replication of Type 2 ATF-deletion mutants was observed in PBMC-derived macrophages. Replication of FIV LTR mutant viruses in specific pathogen free cats is to be assessed.

A. Construction of FIV LTR Mutant Viruses.

Four to 5 nucleotide bases were deleted within the AP-1 (TGACTCA) and ATF (TGACGT) sequences within the U3 domain of the FIV-pPPR provirus and confirmed by DNA sequencing. To generate the mutations within the U3 region of the 3' LTR, a Nde1 (bp 8900)-Sal1 (3' polylinker site) fragment of the FIV-pPPR provirus (cloned in the vector pUC 19) containing orf H and the entire 3' LTR was cloned into the plasmid pGem5Zf+ (Promega Biotech, Madison, Wis., USA) using the restriction sites Nde1 and Sal1 within the plasmid polylinker. The resulting construct was named pNS5 and was used as a template for site-directed deletion mutagenesis. The following oligonucleotides were used for mutagenesis using PCR-mediated overlap extension {Ho, S. N., et al., Gene, 77:51–59 (1989)} of the 3' LTR and construction of the LTR mutant proviruses:

a) FIV-LTR-A derived from the pGem5Zf polylinker and pPPR provirus pb 8898 to bp 8907 (5' GCGTTGG-GAGCTCTCCCATATGAATCC 3') (SEQ ID NO:1);

b) FIV-LTR-B-AP1, bp 9230 to bp 9169 of the FIV-pPPR provirus (5' CTGCTAGCGCTTTAACTATGTGT-TCAGCTGTTTCCATTTATCATTTGTTTGTG ACAG 3') (SEQ ID NO:2);

c) FIV-LTR-C-AP-1, bp 9241 to bp 9184 of the FIV-pPPR provirus (5' GATAAATGGAAACAGCTGAACACAT-AGTTAAAGCGCTAGCAGCTGCTTAACCG 3') (SEQ ID NO:3);

d) FIV-LTR-D which includes a flanking Sal1 site and bp 9468 to bp 9441 of the FIV-pPPR provirus (5' GTCGGTCGACTGCGAAGTTCTCGGCCCGGATT-CCGAGACC3') (SEQ ID NO:4);

e) LTR-B-ATF, bp 183 to bp 126 of the FIV-pPPR provirus (5' CTTACAGTGGAGCAAATTATCATTG-GCAAGCTTTACATAGGATGTGGTTTTGC G 3') (SEQ ID NO:5);

f) LTR-C-ATF, bp 140 to 186 of the FIV-pPPR provirus (5' CCTATGTAAAGCTTGCCAAG-TATAATTTGCTCCACTGTAAGAG 3') (SEQ ID NO:6);

g) LTR-Kas1, bp 370 to 328 of the FIV-pPPR provirus (5' CTGTCGGGCGCCAACTGCGAAGTTCTCG-GCCCGGATTCCGAG 3') (SEQ ID NO:7);

h) LTR-Spe1 which includes a flanking 5' Spe1 site and bp 1 to bp 22 of the FIV-pPPR provirus (5' GGACTAGT-TGGGATGAGTATTGGGACCCTG 3') (SEQ ID NO:8).

Primers FIV-LTR-A, FIV-LTR-D, FIV-LTR-B-AP1, and FIV-LTR-C-AP-1 were used to construct a 3' LTR with a 5 bp (TGACT) deletion of the AP-1 site. The AP-1 deleted 3' LTR was cloned back into pNS5 to create pNS5-AP-1. Primers FIV-LTR-A, FIV-LTR-D, FIV-LTR-B-ATF, and FIV-LTR-C-ATF were used to construct a 3' LTR with a 4 bp (TGAC) deletion of the ATF-1 site. The ATF-deleted 3' LTR was cloned back into pNS5 to created pNS5-ATF. pNS5-AP-1 was used as a template for mutagenesis with primers FIV-LTR-B-ATF and FIV-LTR-C-ATF to construct a 3' LTR with deletions of both the AP-1 and the ATF sites. The AP-1 and ATF deleted 3' LTR was cloned back into pNS5 to create pNS5-AP-1/ATF. Once the LTR deletion(s) was confirmed by dideoxynucleotide sequencing within the pNS5 vector, the Nde1-Sal1 fragment containing the mutated LTR was cloned back into the FIV-pPPR provirus using the Nde1 and Sal1 sites of the FIV-pPPR WT (previously cloned into the plasmid vector pGem 9Zf+) to generate a FIV-pPPR provirus with a mutated 3' LTR. To complete construction of a Type 1 LTR mutant, the mutated LTR was PCR amplified from pNS5 using primers LTR-Kas1 and LTR-Spe1. Using the restriction enzyme sites Spe1 (5' polylinker) and Kas1 (same as Nar1) (bp 360) within the FIV-pPPR provirus, the amplified mutant 5' LTR was cloned into the FIV-pPPR provirus with a mutated 3' LTR to generate a provirus with mutations in both the 5' and 3' LTR i.e., FIV-pPPRΔAP-1, FIV-pPPRΔATF, and FIV-pPPRΔAP-1/ATF (FIG. 1). Mutations within the proviruses were confirmed by dideoxynucleotide sequencing.

Type 2 mutuant proviruses were constructed by the replacement of the 5' LTR in the FIV-pPPR WT provirus with a SV40pr/RU5 hybrid promoter to generate the construct pSVWT-PPR. The SV40pr/RU5 hybrid promoter contains enhancer sequences and the TATA box of the SV40 early promoter in the place of the U3 region of 5' LTR. To create the SV40pr/RU5 hybrid promoter, the following PCR primers were used:
a) SV40-Spe1 which includes flanking Sac1 and Spe1 sites and bp 276 to bp 249 of the SV40 genome (5' GAC-GAGAGCTCACTAGTCCAGCTGTGGAAT-GTGTGTCAGTTAGGG 3') (SEQ ID NO:9);
b) SV40-Bgl2 which includes a flanking Bgl2 site and bp 20 to bp 49 of the SV40 genome (5' CGCAGAGATCTG-CATAAATAAAAAAAATTAGTCAGC-CATGGGGCGGAG 3') (SEQ ID NO:10);
c) RU5-Bgl2 which includes flanking BamH1 and Bgl2 sites and bp 199 to bp 234 of the FIV-pPPR provirus (5' CGAGGATCCAGATCTTTGTGAAACTTC-GAGGAGTCTCTTTGTTGAGGAC 3') (SEQ ID NO:11);
d) RU5-Kas1 which includes a flanking Pst1 site and internal Kas1 (Nar1) and bp 365 to bp 340 of the FIV-pPPR provirus (5' CAGTCGCTGCAGCGGGCGCCAACTGC-GAAGTTCTCGGC 3') (SEQ ID NO:12).

Figure 3A:
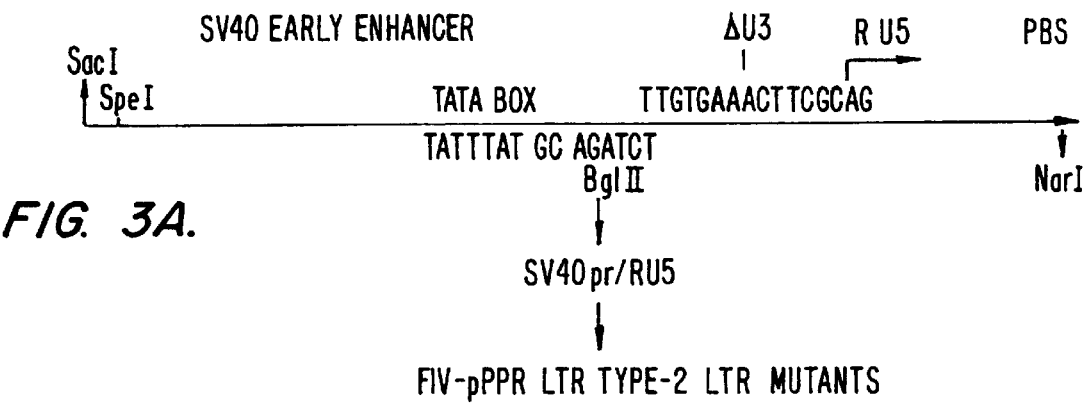
FIGS. 3A to 3C schematically present the strategy, starting from FIG. 3A. SV40pr/RU5 is cloned into the LTR mutants of FIG. 3B. pSV-pPPRΔAP-1, pSV-pPPRΔATF and pSV-pPPRΔAP-1/ATF.
Figure 3B:
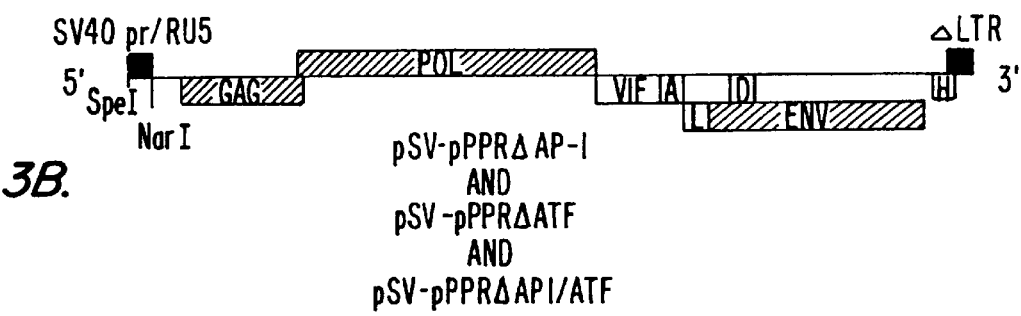
Figure 3C:
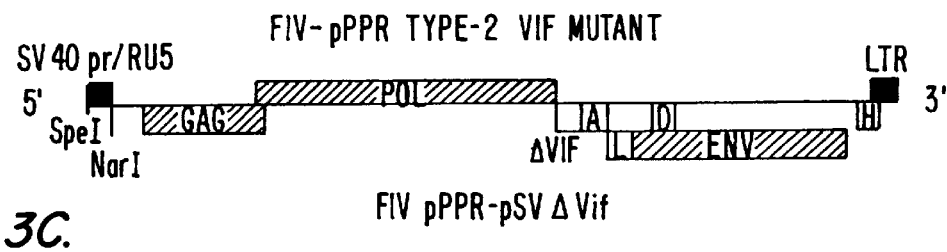

The RU5 region including bp −1 to −16 of the U3 region of the 5' LTR of the FIV-pPPR provirus was PCR amplified using primers RU5-Bgl2 and RU5-Kas1 and cloned into a transient chloramphenicol acetyltransferase (CAT) expression vector (p22A2s) {Sparger, E. E., et al., *Virol.*, 187:165–177 (1992)} using restriction enzyme sites BamH1 and Pst1 (polylinker of p22A2s) to yield the construct ΔU3-CAT. Next, the SV40 early promoter, including enhancer sequences and TATA box was PCR amplified using primers SV40-Spe1 and SV40-Bgl2, and cloned into ΔU3-CAT using restriction enzyme sites Bgl2 and Sac1 to yield the recombinant plasmid pSVRU5 containing the SV40pr/RU5 hybrid promoter (FIG. 3). The SV40pr/RU5 hybrid promoter was digested from pSVRU5 using restriction enzyme sites Spe1 and Kas1 (Nar1 ) and cloned into the FIV-pPPR WT provirus to yield the construct pSV-pPPR WT. Next, the AP-1 deleted 3' LTR was cloned from pNS5-AP-1 into pSV-pPPR WT using restriction enzyme sites Nde1 and Sal1 to yield the construct pSV-pPPRΔAP-1 (FIG. 3). Similarly the ATF-deleted LTR and AP-1/ATF-deleted LTR were cloned from pNS5-ATF and pNS5-AP-1/ATF respectively, into pSV-pPPR WT to yield constructs pSV-pPPRΔATF and pSV-pPPRΔAP-1/ATF (FIG. 3). The presence of the SV40pr/RU5 hybrid promoter and 3' LTR deletions were confirmed by dideoxynucleotide sequencing.

B. Characterization of FIV LTR Mutant Viruses in Primary Feline PBMC.

Figure 2:
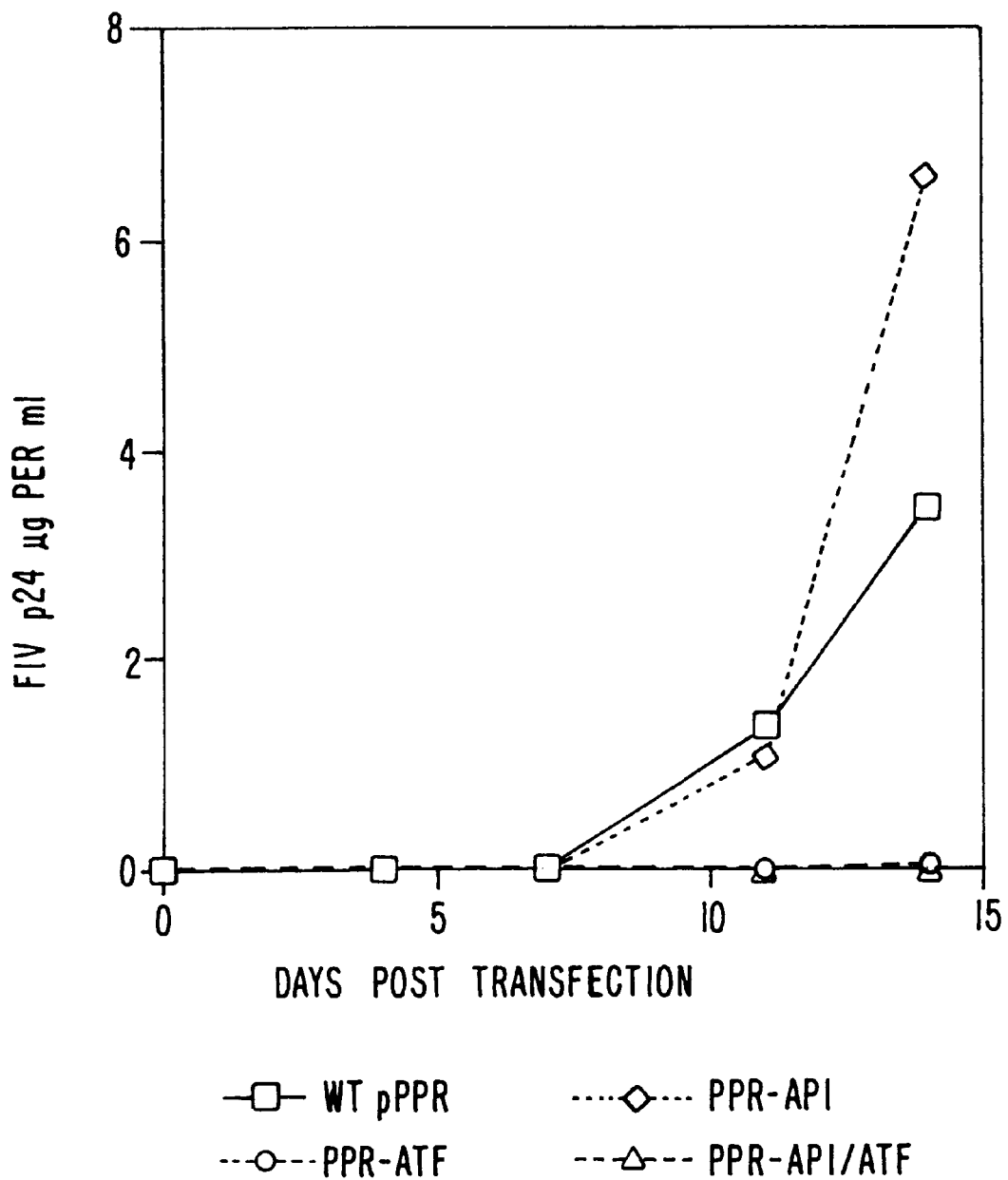
FIG. 2 graphically presents the expression of FIV-pPPR LTR Type 1 mutants in feline PBL post transfection.

In ongoing studies, CrFK cells, a feline adherent cell line, were electroporated with a FIV LTR mutant provirus construct (10 µg) described in FIG. 1 or with wild type (WT) FIV-pPPR and cocultivated with primary feline PBMC 24 hours later. Cocultivated PBMC were separated from CrFK cells 24 hours later and maintained in culture up to 4 weeks post transfection. Infected cell culture supernatants were harvested every 3 to 4 days and tested by a FIV p24 antigen capture ELISA (FIG. 2). Preliminary data indicates that deletion of the AP-1 site results in minimal reduction of replication of FIV-pPPR in PBL based on FIV-p24 antigen concentration in infected cell supernatants, whereas deletion of the ATF site produces a moderate but significant reduction of virus replication in feline PBL. Deletion of both the AP-1 and ATF sites results in almost a complete reduction of virus replication in feline PBL post transfection of proviral DNA. Replication kinetics of AP-1 and ATF mutant viruses are currently being assessed in infection studies in feline PBL and primary feline macrophages (see below).

Figure 4:
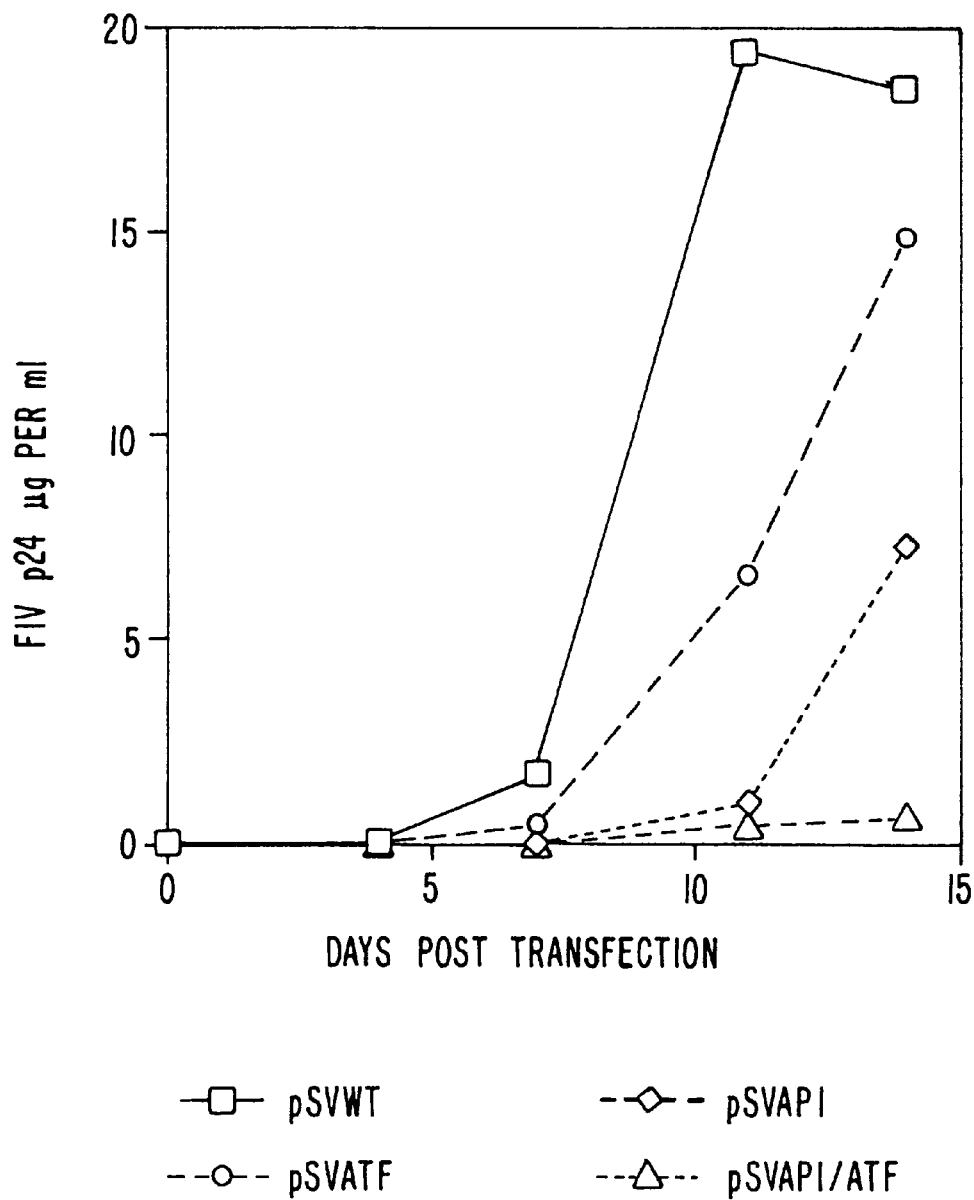
FIG. 4 graphically presents the expression of FIV-pPPR LTR Type 2 mutants in feline PBL post transfection.
Figure 5:
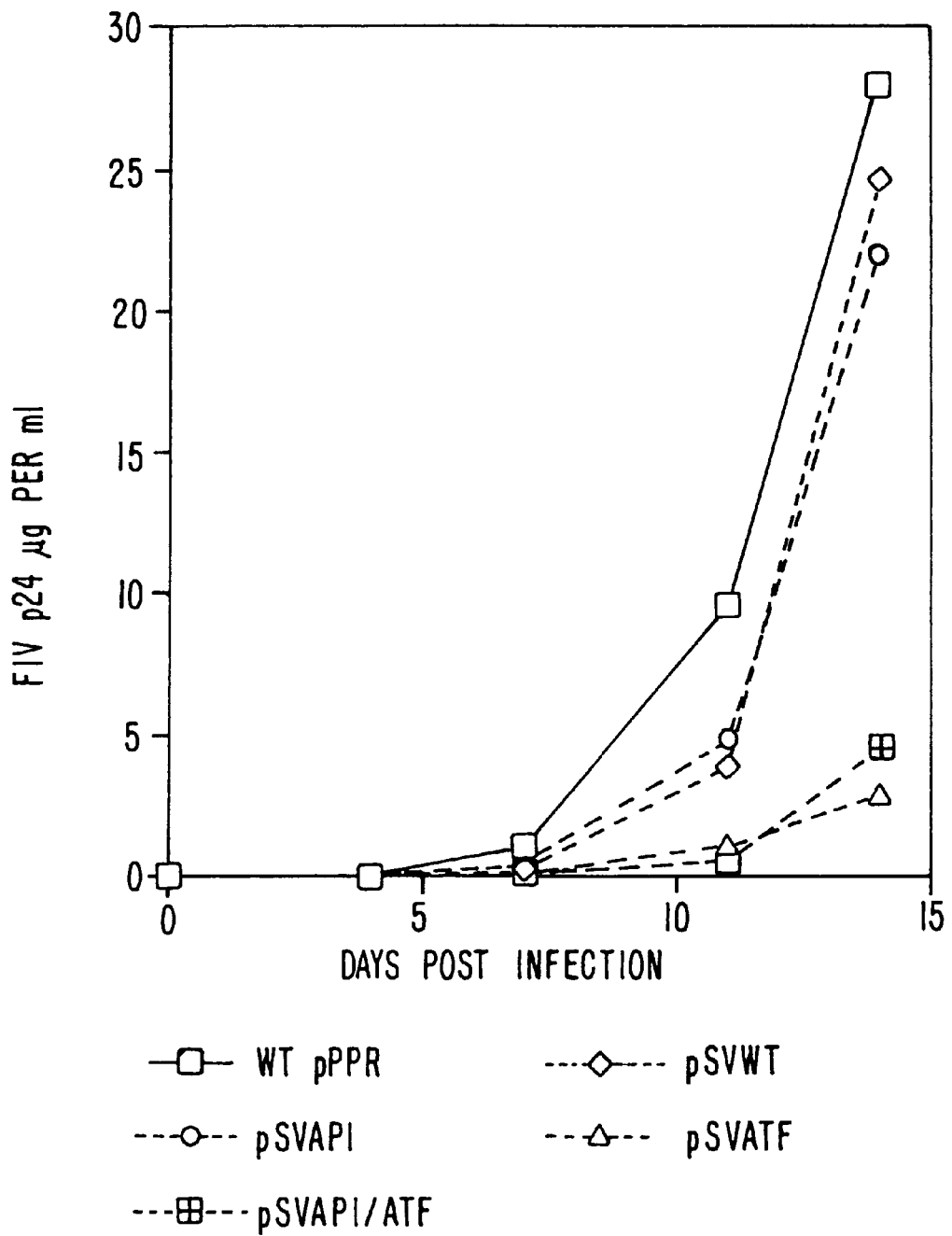
FIG. 5 graphically presents the replication of FIV-pPPR LTR Type 2 mutants in feline PBL.
Figure 6:
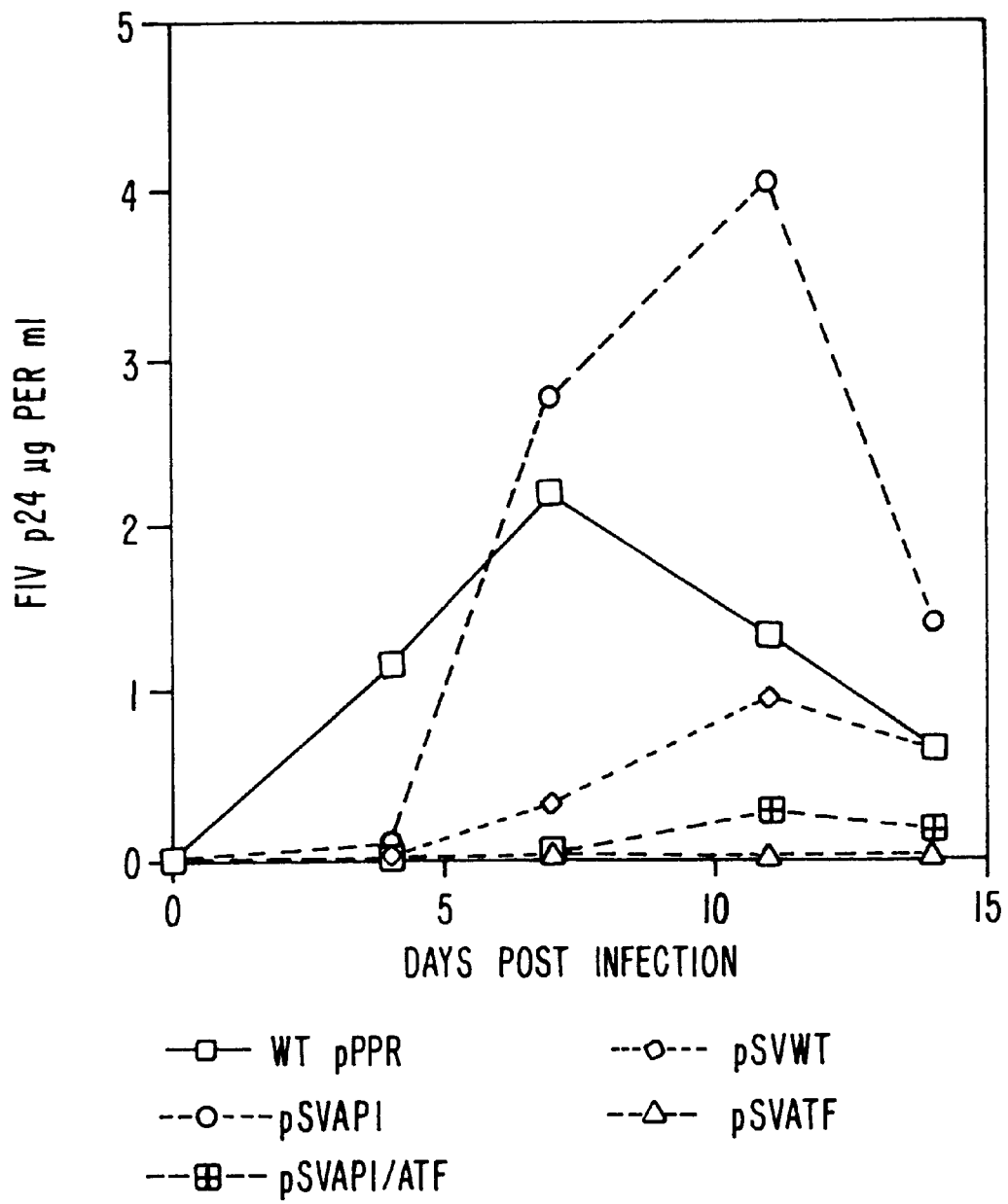
FIG. 6 graphically presents the replication of FIV-pPPR LTR Type 2 mutants in feline macrophages.

Provirus constructs (WT and mutant) driven by a SV40pr/RU5 promoter (FIG. 3) and constructed to generate LTR mutant viruses, were found to be infectious in feline PBMC (FIG. 4). Transfection of pSV-PPRΔATF, and pSV-PPRΔAP1/ATF into CrFK cells and cocultivation with feline PBMC resulted in greater virus production when compared with transfection of proviruses containing both a mutated 5' and 3' LTR (FIG. 2). These pSV constructs have produced higher titered LTR mutant virus stocks which have been used for infection and replication studies in PBMC and macrophages. In studies where $4 \times 10^6$ PBL are inoculated with 100 $TCID_{50}$ of a titered virus stock, viruses containing a deletion of the ATF site were able to replicate in PBL but with slower kinetics (FIG. 5). A similar reduction in replication was also observed in feline macrophages inoculated with LTR mutant viruses containing a deletion of the ATF site (FIG. 6). Using polymerase chain reaction (PCR) amplification of viral DNA from infected PBMC, nucleotide sequencing of both 5' and 3' LTR regions confirmed the presence of appropriate deletions in the various LTR mutant virus stocks.

C. Inoculation of Cats with FIV-pPPR LTR Mutant Viruses

Groups of specific pathogen free (SPF) cats (n=5) were inoculated intraperitoneally (IP) with $10^3$ $TCID_{50}$ from one of the following FIV-pPPR LTR WT or mutant virus stocks: pSVWT, pSVpPPRΔAP1, pSVpPPRΔATF, or pSVpPPRΔAP1/APF. One group of 4 control cats was inoculated with uninfected tissue culture fluid. These cats have been followed by semiquantitative virus isolation for an estimation of virus load/virus replication following infection with the mutant viruses (Table 1). At each time point noted, $10^6$ PBMC harvested from each cat, and ten-fold dilutions of PBMC were cocultivated with SPF PBMC and assayed for virus production by an FIV p24 antigen capture assay up to 28 days and some times longer, post cultivation. Cat PBMC preparations found negative for FIV p24 negative for all PBMC dilutions were considered virus negative (−) (Table 1). Viremia in cats whose PBMC cultures were FIV p24 positive was expressed as the lowest concentration of cells from which virus could be isolated (Table 1).

Observations from this experimental inoculation study indicate that LTR mutant viruses containing a deletion of the ATF site were significantly attenuated in their capacity for virus replication and induction of virus load in the inoculated cat. Viremia was rarely detectable in cats inoculated with FIV-pPPR mutant containing a deletion of both the AP-1 and ATF sites yet four out of the five inoculated cats seroconverted by 16 weeks post infection. Although viremia was more frequently detected in cats inoculated with FIV-pPPR mutant virus containing a single deletion of the ATF site, virus was often not detected in PBMC cultures until 28 days or later post harvest and cultivation. During later stages of infection (18 to 33 weeks post infection) with the ATF-deletion mutant, viremia was easily detected in four out of the five inoculated cats. In virus positive cats inoculated with WT FIV-pPPR (pSV-WT) virus or the AP-1 deletion mutant virus, virus was consistently isolated from PBMC by 14 to 18 days after harvest. A significant viremia was observed during the early stages (up to 18 weeks) in all cats inoculated with the AP-1 deletion mutant virus and was no less than that observed in cats inoculated with WT virus. This semiquantitative virus isolation data indicated that deletion of the AP-1 site did not restrict replication of FIV-pPPR in vivo. Deletion of the ATF site and especially deletion of the ATF and AP-1 sites restricted virus replication in vivo as well as in vitro. Virus load in these inoculated cats can be assessed by QC-RT PCR and viral genotype in cultured and uncultured PBMC are being examined by DNA sequencing of viral LTR sequences amplified by PCR.

TABLE 1

Detection of Virus in SPF Cats Inoculated With FIV-pPPR LTR Mutant Viruses

| Animal | Virus Inoculum | Virus Isolation Weeks Post Inoculum | | | | | |
|---|---|---|---|---|---|---|---|
| | | 2 | 4 | 8 | 12 | 18 | 33 |
| 256 | pSVWT | $-^a$ | $10^6$ | $10^6$ | $10^6$ | $10^5$ | - |
| 267 | pSVWT | $10^6$ | $10^5$ | $10^4$ | $10^4$ | $10^4$ | $10^5$ |
| 274 | pSVWT | - | - | - | - | - | - |
| 293 | pSVWT | $10^6$ | $10^5$ | $10^6$ | $10^5$ | $10^5$ | $10^6$ |
| 298 | pSVWT | $10^6$ | $10^6$ | $10^5$ | $10^4$ | $10^5$ | $10^3$ |
| 257 | pSVΔAP1 | $10^6$ | $10^6$ | $10^5$ | $10^5$ | $10^6$ | $10^5$ |
| 268 | pSVΔAP1 | $10^6$ | - | $10^3$ | $10^4$ | $10^5$ | $10^6$ |
| 275 | pSVΔAP1 | $10^6$ | $10^6$ | $10^4$ | $10^3$ | $10^4$ | - |
| 294 | pSVΔAP1 | $10^6$ | $10^5$ | $10^5$ | $10^5$ | $10^4$ | $10^6$ |
| 299 | pSVΔAP1 | - | $10^5$ | $10^5$ | $10^5$ | $10^4$ | - |
| 265 | pSVΔATF | - | - | - | - | $10^4$ | $10^5$ |
| 269 | pSVΔATF | $10^6$ | - | $10^{5b}$ | $10^5$ | $10^5$ | $10^5$ |
| 276 | pSV-ATF | $10^{6b}$ | - | $10^{6b}$ | $10^{5b}$ | $10^{6b}$ | $10^5$ |
| 295 | pSVΔATF | $10^{6b}$ | $10^5$ | - | - | - | - |
| 301 | pSV-ATF | $10^{6b}$ | $10^5$ | - | $10^{5b}$ | $10^4$ | $10^4$ |
| 266 | pSVΔAP1/ATF | $10^{6b}$ | - | - | - | - | - |
| 273 | pSVΔAP1/ATF | $10^6$ | $10^5$ | - | - | - | - |
| 292 | pSVΔAP1/ATF | - | - | - | - | $10^{6b}$ | - |
| 296 | pSVΔAP1/ATF | - | - | - | - | - | - |
| 302 | pSVΔAP1/ATF | - | - | - | - | - | - |
| 144 | Control | - | - | - | - | - | - |
| 145 | Control | - | - | - | - | - | - |
| 146 | Control | - | - | - | - | - | - |
| 147 | Control | - | - | - | - | - | - |

[a]Virus isolations were performed by cultivation of serial dilutions of harvested PBMC from each cat at each time point and carried out for 28 days with the exception of time point 18 weeks PI which was carried out for 56 days. The symbol (-) indicates virus was not isolated from any of PBMC dilutions cultured whereas a number value represents the lowest concentration of cells from which virus could be isolated by day 28 (56 for 18 weeks PI) in culture.
[b]Virus was not detected until day 28 or later in culture.

D. Challenge of Cats Infected with FIV-pPPR LTR Mutant Viruses with Biological FIV-PPR-VIRUS To assess for protective immunity induced by infection with attenuated FIV virus, cats (5) inoculated with the ATF/AP-1 deletion mutant of FIV-pPPR as well as uninfected SPF control cats (4) were challenged first at 33 weeks post infection with pSVΔAP1/ATF with 10 animal infectious doses (AID) of a previously titered virus stock of biological FIV-pPPR virus. Biological FIV-PPR has been previously shown to be moderately pathogenic (Part 1) and is the biological isolate from which molecular FIV-pPPR was isolated. Viremia was not detected in any of the inoculated cats including the previously uninfected (unvaccinated) controls by 8 weeks post infection with this dose of challenge virus and challenge inoculum was therefore considered inadequate (data not shown). In a second study, these same cats were re-challenged 14 weeks later with 100 $TCID_{50}$ of the same virus stock of biological FIV-PPR and were assessed for protection viremia with challenge virus by semi-quantitative virus isolations and by direct nucleotide sequencing of LTR sequences amplified by PCR from cultivated PBMC used for virus isolation. By 3 weeks post challenge, 3 out of the 4 unvaccinated control cats were significantly viremic, while viremia was detected in 1 of the 5 cats previously inoculated with pSVΔAP1/ATF (Table 3). At 5 weeks and 8 weeks post challenge, virus could be isolated by 15 to 18 days in culture and from lower concentrations of cells ($10^3$ to $10^5$) from all 4 cats in the control group (not previously infected or vaccinated with a FIV LTR mutant).

At 5 weeks and 8 weeks post challenge, virus was isolated relatively quickly (by day 22) from 1 out of 5 cats previously inoculated with pSVΔAP1/ATF and was identified as challenge (or possibly revertant) virus based on DNA sequence of PCR-amplified LTR domains from genomic DNA extracted from cultivated PBMC used in the virus isolation. For 1 cat virus, isolation was negative and for 3 cats from the same group, virus isolation cultures from were not virus positive until day 25 to 28 in culture and the isolated viruses were characterized as pSVΔAP1/ATF (mutant) by LTR DNA sequence as just described. Interestingly, the cat (#296) in the pSVΔAP1/ATF-inoculated/vaccinated group which did not resist challenge was the only cat in this group that never seroconverted post inoculation with pSVΔAP1/ATF (Table 2). Lack of seroconversion suggests that this cat either harbored an extremely low virus load post inoculation with pSVΔAP1/ATF or that established infection with pSVΔAP1/ATF did not occur. This finding might suggest that an established infection with attenuated pSVΔAP1/ATF as marked by seroconversion is necessary for induction of protective immunity against infection with WT biological FIV-PPR.

Preliminary results indicate (Table 3) that as of 8 weeks post challenge, 4 out of 5 cats infected (vaccinated) with pSVΔAP1/ATF have resisted infection/challenge with a biological FIV-PPR virus inocula capable of inducing a significant viremia by 3 weeks post challenge in uninfected (unvaccinated) control cats. While definitive conclusions will be made after viremia in PBMC as well as lymphoid tissues is assessed in all cats at later time points post challenge, the existing data does indicate that infection with pSVΔAP1/ATF at least delays the onset of viremia post challenge with WT biological FIV-PPR and may induce protection against infection.

TABLE 2

Dectection of FIV p24 Antibody In SPF Cats Inoculated with FIV-pPPR LTR Mutant Viruses

| Animal | Virus Inoculum | Serum Antibody[a] Weeks Post Inoculum | | | | | | | | | |
|---|---|---|---|---|---|---|---|---|---|---|---|
| | | 0 | 2 | 4 | 6 | 8 | 10 | 12 | 14 | 16 | 33 |
| 256 | pSVWT | - | - | - | - | + | + | + | + | + | + |
| 267 | pSVWT | - | - | - | + | + | + | + | + | + | + |
| 274 | pSVWT | - | - | - | - | - | - | - | - | - | - |
| 293 | pSVWT | - | - | - | + | + | + | + | + | + | + |
| 298 | pSVWT | - | - | - | - | - | + | + | + | + | + |
| 257 | pSVΔAP1 | - | - | - | + | + | +/- | + | + | + | + |
| 268 | pSVΔAP1 | - | - | - | + | + | + | + | + | + | + |

TABLE 2-continued

Dectection of FIV p24 Antibody In SPF Cats Inoculated with
FIV-pPPR LTR Mutant Viruses

| Animal | Virus Inoculum | Serum Antibody[a] Weeks Post Inoculum | | | | | | | | |
|---|---|---|---|---|---|---|---|---|---|---|
| | | 0 | 2 | 4 | 6 | 8 | 10 | 12 | 14 | 16 | 33 |
| 275 | pSVΔAP1 | − | − | − | +/−[b] | − | +/− | + | + | + | + |
| 294 | pSVΔAP1 | − | − | − | + | + | + | + | + | + | + |
| 299 | pSVΔAP1 | − | − | − | + | + | + | + | + | + | + |
| 265 | pSVΔATF | − | − | − | − | − | − | − | +/− | + | + |
| 269 | pSVΔATF | − | − | − | + | + | + | + | + | + | + |
| 276 | pSVΔATF | − | − | − | +/− | +/− | + | + | + | + | + |
| 295 | pSVΔATF | − | − | − | − | − | − | − | − | − | − |
| 301 | pSVΔATF | − | − | − | + | + | + | + | + | + | + |
| 266 | pSVΔAP1/ATF | − | − | − | + | + | + | + | + | + | + |
| 273 | pSVΔAP1/ATF | − | − | − | + | + | + | + | + | + | + |
| 292 | pSVΔAP1/ATF | − | − | − | − | +/− | +/− | +/− | +/− | + | + |
| 296 | pSVΔAP1/ATF | − | − | − | − | − | − | − | − | − | − |
| 302 | pSVΔAP1/ATF | − | − | − | − | − | − | − | − | + | + |
| 144 | Control | − | − | − | − | − | − | − | − | − | − |
| 145 | Control | − | − | − | − | − | − | − | − | − | − |
| 146 | Control | − | − | − | − | − | − | − | − | − | − |
| 147 | Control | − | − | − | − | − | − | − | − | − | − |

[a]Serum antibody to recombinant FIV p24 was assayed by an FIV p24 antibody ELISA.
[b]+/− designates an indeterminate result.

TABLE 3

Detection of Virus In SPF Cats Infected with FIV-pPPR LTR
Mutant Viruses and Challenged with Biological FIV-PPR

| Animal | Virus Inoculum | Virus Isolation Weeks Post Challenge (Post Infection) | | | |
|---|---|---|---|---|---|
| | | 0 (42)[a] | 3 (50) | 5 (52) | 8 (55) |
| 266 | pSVΔAP1/ATF | −[b] | $10^5$ (ND)[c] | $10^5$ (Mut)[c] | $10^5$ (Mut)[c] |
| 273 | pSVΔAP1/ATF | − | − | $10^4$ (ND)[c] | $10^4$ (Mut)[c] |
| 292 | pSVΔAP1/ATF | − | − | − | − |
| 296 | pSVΔAP1/ATF | − | − | $10^6$ (WT) | $10^6$ (WT) |
| 302 | pSVΔAP1/ATF | − | − | $10^5$ (ND)[c] | $10^3$ (Mut)[c] |
| 144 | Control | − | − | $10^6$ | $10^4$ |
| 145 | Control | − | $10^4$ | $10^3$ | $10^3$ |
| 146 | Control | − | $10^4$ | $10^4$ | $10^3$ |
| 147 | Control | − | $10^3$ | $10^3$ | $10^4$ |

[a]Number above reflects weeks post challenge with biological FIV-PPR whereas lower number in parentheses designates time post infection with WT or mutant virus.
[b]Virus isolations were performed on serial dilutions of harvested PBMC from each cat at each time point as described for Table 1 except isolations carried out for 42 days. The symbol (−) indicates virus was not isolated from any of PBMC dilutions cultured whereas a number value represents the lowest concentration of cells from which virus could be isolated by day 42 in culture.
[c]Virus was not detected until day 28 or later in culture. Virus genotype is noted in parentheses and was determined by nucleotide sequencing of amplified LTR sequences from cultivated PBMC. Mut indicates isolated virus was mutant and was identified as pSVΔAP1/ATF by LTR DNA sequence and WT indicates that the isolated virus was wild type (challenge). ND indicates that sequence is not determined at this time.

Example 3

Immunization of Cats with Attenuated Molecularly Cloned Isolates of FIV via DNA Injection A. Production of FIV Proviral Plasmid DNA for Experimental Inoculation of SPF Cats.

To determine the optimal concentration of proviral plasmid DNA for establishing viremia upon intramuscular (IM) injection, production of large amounts of DNA free of bacterial endotoxin was necessary. The recombinant FIV-pPPR plasmid DNA containing the proviral DNA (obtained from Dr. John Elder, Scripps Research Institute, La Jolla, Calif., USA) was prepared as described in Phillips, T. R., et al., *J. Vir.*, 64(10):4605–4613 (1990). The starting plasmid FIV-pPPR stock was expanded in STBL2™ *E. coli* strains (Gibco BRL, Gaithersburg, Md., USA). Plasmid DNA was purified by centrifugation to equilibrium in cesium chloride-ethidium bromide gradients twice. Plasmid growth and purification are described in Sambrook, et al., *Molecular Cloning: A Laboratory Manual*, (Cold Spring Harbor Laboratory Press, 2d ed., 1989). DNA was resuspended in distilled water and adjusted to 500 mg/ml. The yield was about 300 μg–500 μg per 500 ml of culture.

B. Inoculation of SPF Cats with Molecularly Cloned FIV Proviral DNA

To determine the optimal concentration of infectious proviral plasmid DNA for establishing a FIV-associated viremia upon IM injection, 3 groups (n=3) of specific pathogen free (SPF) cats were inoculated IM with either 300 μg, 100 μg, or 30 μg of plasmid DNA containing the infectious molecular clone, FIV-pPPR plasmid was resuspended in standard sterile physiological saline. A fourth group of cats were inoculated intradermally (ID) with 30 μg of FIV-pPPR plasmid DNA for the same composition. One inoculation shot per cat was administered. Inoculation with 100 to 300 μg of infectious FIV-pPPR proviral DNA consistently resulted in a viral infection detectable by both viral antibody and virus isolation from PBMC (TABLES 4 and 5). Inoculation with 30 μg of proviral DNA resulted in an infection detectable by serology {using the procedure described Sparger, E. E., et al., *Virol.*, 205:546–553 (1994)} and virus isolation in 50% of the inoculated cats {using the procedure described Sparger, E. E., et al., *Virol.*, 205:546–553 (1994)}. The appearance of viral antibody and virus detectable by virus isolation, using procedures as previously described was delayed in cats inoculated with 30 μg when compared with time of onset in cats inoculated with either 100 μg or 300 μg of proviral DNA. Except for one cat displaying a transient fever 3 hours post inoculation, intramuscular and intradermal injection of plasmid proviral DNA was well tolerated by the cats. This study indicates that 100 μg of proviral DNA is sufficient to induce an FIV-pPPR infection with viremia kinetics similar to that observed with inoculation of live virus preparations of FIV-PPR. This study also suggests that infectious molecularly cloned proviral DNA may replace virion preparations produced in mammalian cell culture as inocula for pathogenesis and immunization studies with molecularly cloned isolates of FIV.

TABLE 4

Detection of FIV p24 Antibody In SPF Cats Inoculated With Molecularly Cloned FIV-pPPR Proviral DNA

| Animal | Inoculum and Route | Serum Antibody[a] Weeks Post Inoculum | | | | | | | | |
|---|---|---|---|---|---|---|---|---|---|---|
| | | 0 | 2 | 4 | 6 | 8 | 10 | 12 | 14 | 15 |
| 479 | 300 µg IM[b] | − | − | − | + | + | + | + | + | + |
| 521 | 300 µg IM | − | − | − | − | + | + | + | + | + |
| 522 | 300 µg IM | − | − | − | − | +/−[c] | + | + | + | + |
| 337 | 100 µg IM | − | − | − | +/− | + | + | + | + | + |
| 438 | 100 µg IM | − | − | − | +/− | + | + | + | + | + |
| 523 | 100 µg IM | − | − | − | − | − | +/− | + | + | + |
| 333 | 30 µg IM | − | − | − | − | − | − | + | + | + |
| 477 | 30 µg IM | − | − | − | − | +/− | − | − | − | − |
| 499 | 30 µg IM | − | − | − | − | +/− | + | + | + | + |
| 336 | 30 µg ID[d] | − | − | − | − | − | + | + | + | + |
| 473 | 30 µg ID | − | − | − | − | − | − | − | − | − |
| 536 | 30 µg ID | − | − | − | − | − | − | − | − | − |

[a]Serum antibody to recombinant FIV p24 was assayed by an FIV p24 antibody ELISA.
[b]IM designates intramuscular injection.
[c]+/− designates an indeterminate result.
[d]ID designates intradermal injection.

TABLE 5

Detection of Virus In SPF Cats Inoculated With Molecularly Cloned FIV-pPPR Proviral DNA

| Animal | Inoculum and Route | Virus Isolation[a] Weeks Post Inoculum | | | | |
|---|---|---|---|---|---|---|
| | | 2 | 4 | 8 | 12 | 15 |
| 479 | 300 µg IM | − | + | − | + ($10^5$)[b] | + ($10^3$) |
| 521 | 300 µg IM | − | + | − | + ($10^6$) | + ($10^5$) |
| 522 | 300 µg IM | − | + | − | + ($10^5$) | + ($10^5$) |
| 337 | 100 µg IM | − | + | + | + ($10^5$) | + ($10^6$) |
| 438 | 100 µg IM | − | + | + | + ($10^5$) | + ($10^4$) |
| 523 | 100 µg IM | − | − | + | + ($10^5$) | + ($10^5$) |
| 333 | 30 µg IM | − | − | + | + ($10^6$) | + ($10^5$) |
| 477 | 30 µg IM | − | − | − | − | − |
| 499 | 30 µg IM | − | − | + | − | + ($10^6$) |
| 336 | 30 µg ID | − | − | + | − | + ($10^6$) |
| 473 | 30 µg ID | − | − | − | − | − |
| 536 | 30 µg ID | − | − | − | − | − |

[a]PBMC were harvested from each cat, stimulated with concanavalin A for 3 days, and cultivated in the presence of IL-2. Supernatant was collected twice weekly from PBMC cultures for 4 weeks post cultivation and assessed for FIV-p24 by an FIV p24 capture ELISA.
[b]Virus isolations were performed on serial dilutions of harvested PBMC from each cat at this time point. The value in the parentheses represents the lowest concentration of cells from which virus could be isolated.

Example 4

Immunization of Cats with an Attenuated Molecularly Cloned FIV DNA Plasmid

Introduction

A FIV vaccine consisting of the gene deleted (attenuated) PPR virus wherein a mutant stock was prepared by removing pSVAP1/ATF genes. This was prepared as a DNA plasmid free of bacterial endotoxin which was purified twice by centrifugation in cesium chloride-ethidium bromide gradient. Alternately the DNA may also be purified by use of a chromatography column by selected buffers and then the DNA removed by high salt buffer. The resultant DNA can then be precipitated out by various solutions such as for example isopropanol and resuspended in concentrated form.

Cat Immunization Studies

A vaccine was prepared containing 500 µg of DNA consisting of the double gene deleted PPR virus (pSV AP1/ATF).

As a control, 500 µg of FIV proviral DNA (pSVWT PPR) per cat dose was also prepared.

Six cats were inoculated intramuscularly, each with 500 µg of the DNA vaccine. Five additional cats were each inoculated intramuscularly with 500 µg of proviral DNA as a control of the gene deleted DNA vaccine.

Following inoculation, blood samples were taken from each cat every two weeks and evaluated for the presence of FIV RNA or DNA in the peripheral monocyte cells using procedure as described in Diehl, L. J., et al., *J. Virol.*, 69:2328–2332 (1995) and Sparger, E. E., et al., *Virol.,* 205:546–553 (1994). Plasma was also evaluated for antibodies against core antigen (p24 gag), envelope, and whole virus using procedure as described in Sparger, E. E., et al., *Virol.,* 205:546–553 (1994).

Results

As may be noted in TABLE 6, all of the control cats inoculated with the proviral (pSVWT PPR) preparation expressed FIV viruses and developed antibodies. No changes in blood cell counts or other clinical responses were noted. The viral expression began as early as 3 weeks following inoculation.

By comparison, only three of the six attenuated plasmid DNA vaccinated cats had detectable FIV virus, and this response was delayed up to five to seven weeks after inoculation indicating that the gene deletion resulted in delayed onset to FIV virus production. However, five of the six cats developed anti p24 antibodies demonstrating an immunologic response to the vaccine. Four to eight weeks post challenge with virulent molecularly cloned PPR virus, five of six cats vaccinated with the proviral pSVΔAP1/ATF virus were seronegative for wild type challenge virus. Post challenge virus isolation was confirmed by PCR and/or sequence. Virus load from attenuated plasmid DNA vaccinated cats was generally 10–100 times less than with wild type controls. Generally, there was no amplification of virus after challenge when compared to non-vaccinated/inoculated cats.

TABLE 6

| Cat No. | Inoculum | Pre-Challenge Virus Recovery | Antibody Response | Post Challenge Virus Recovery | Post Challenge Virus Load (# Infected cells per 1 million cells) |
|---|---|---|---|---|---|
| 468 | pSV AP1/ATF | No | Yes | AP1/ATF | <1 |
| 479 | pSV AP1/ATF | Yes | Yes | None | <1 |
| 481 | pSV AP1/ATF | Yes | Yes | AP1/ATF | 10 |
| 487 | pSV AP1/ATF | No | No | AP1/ATF | <1 |

TABLE 6-continued

| Cat No. | Inoculum | Pre-Challenge Virus Recovery | Antibody Response | Post Challenge Virus Recovery | Post Challenge Virus Load (# Infected cells per 1 million cells) |
|---|---|---|---|---|---|
| 488 | pSV AP1/ATF | Yes | Yes | AP1/ATF | 1 |
| 491 | pSV AP1/ATF | No | No | Wild Type | 10 |
| 469 | pSV WT | Yes | Yes | Wild Type | 10 |
| 478 | pSV WT | Yes | Yes | Wild Type | 10 |
| 480 | pSV WT | Yes | Yes | Wild Type | 10 |
| 482 | pSV WT | Yes | Yes | Wild Type | >1000 |
| 489 | pSV WT | Yes | Yes | Wild Type | 100 |
| 470 | Control | Yes | Yes | Wild Type | Not Done |
| 471 | Control | Yes | Yes | Wild Type | <1 |
| 472 | Control | Yes | Yes | Wild Type | Not Done |
| 484 | Control | Yes | No | Negative | Not Done |
| 486 | Control | Yes | Yes | Wild Type | <1 |

Example 5

Construction and Characterization of Additional FIV-pPPR LTR Mutant Viruses

To construct the Type 1 and Type 2 LTR mutants FIV-pPPRΔ4 and pSVpPPRΔ4, the following primers were used:
a) FIV-LTR-A derived from the pGem5Zf polylinker and pPPR provirus bp 8898 to bp 8907. (5' GCGTTGG-GAGCTCTCCCATATGAATCC 3') (SEQ ID NO: 1);
b) FIV-LTR-D which includes a flanking Sall site and bp 9468 to bp 9441 of the FIV-pPPR provirus. (5' GTCG-GTCGACTGCGAAGTTCTCGGCCCGGAT-TCCGAGACC 3') (SEQ ID NO: 4).
c) LTR Asc Forward includes flanking Asc1 site and bp 9278 to 9297 of the FIV-pPPR provirus. (5' GTCGGGCGCGC-CATAATTTGCTCCACTGTAAG 3') (SEQ ID NO: 13);
d) LTR Asc Reverse includes a flanking Asc1 and Sall sites and bp 9205 to 9184 of the FIV-pPPR provirus. (5' GTCGGTCGACGGCGCGCCTGTTCAGCT-GTTTCCATTTATC 3') (SEQ ID NO: 14);
e) LTR-Kas1, bp 370 to 328 of the FIV-pPPR provirus (5' CTGTCGGGCGCCAACTGCGAAGTTCTCG-GCCCGGATTCCGAG 3'); (SEQ ID NO: 7)
f) LTR-Spe1 which includes a flanking 5' Spe1 site and bp 1 to bp22 of the FIV-pPPR provirus. (5' GGACTAGT-TGGGATGAGTATTGGGACCCTG 3') (SEQ ID NO: 8).

To construct a Type 1 FIV-pPPR LTR mutant FIV-pPPRΔ4, 72 bases within the 3' (bp 9206 to 9277) and the 5' (bp 92 to 163) LTR domains were deleted using PCR cloning to remove the AP-1 and ATF sites and intervening sequence including duplicated C/EBP sites and a single AP-4 site. First, a 342 bp fragment (bp 8898 to bp 9205) was PCR amplified from wild type plasmid FIV-pPPR using primers FIV-LTR-A and LTR Asc Reverse. This PCR product was digested with Nde1 and Sall and cloned into pGem 5Zf to generate plasmid pGemF-1. Next, a 213 bp fragment (bp 9278 to bp 9468) was PCR amplified from wild type FIV-pPPR using primers LTR Asc Forward and FIV-LTR-D. This PCR product was digested with Asc1 and Sall and cloned into Asc1 and Sall-digested pGemF-1 to produce plasmid pGemΔ4. Plasmid pGemΔ4 encodes the 3' terminal subgenomic fragment (bp 8898 to bp 9468) of FIV-pPPR which now includes a 3' LTR containing a deletion of 72 bases replaced by an imperfect (7 bases only) Asc1 site. Sequencing of the DNA insert of pGemΔ4 confirmed the 72 bp deletion replaced by an imperfect 7 bp Asc1 site rather than the expected 8 bp Asc1 site. The 512 bp insert of pGemΔ4 was digested with Nde1 and Sall and cloned into wild type FIV-pPPR (in pGem 9Zf) to replace its 3' terminal Nde1-Sall domain to generate plasmid FIV-pPPR 3'Δ4. The deleted LTR was next amplified from pGemΔ4 using primers LTR-Kas1 and LTR-Spe1 and digested with Spe1 and Kas1. The Kas1-Spe1 digested mutant LTR was then cloned into Kas1-Spe1-digested FIV-pPPR 3'Δ4 to replace its WT 5' LTR and to generate Type 1 LTR mutant FIV-pPPRΔ4 (LTR mutant with both 3' and 5' LTR deletions). To construct a Type-2 LTR mutant pSVpPPRΔ4 (pSVΔ4), the 512 bp insert of pGemΔ4 was digested with Nde1 and Sall and cloned into pSV-pPPR WT to replace the 3' terminal 576 bp Nde1 to Sall fragment of pSV-pPPR WT. The 5' pSV40/RU5 and 3' LTR domains were nucleotide sequenced to confirm the 72 bp deletion and 7 bp Asc1 site in the 3' LTR and SV40 promoter and enhancer sequences in the 5' SV40/RU5 domain of pSVΔ4.

To assess the infectivity and replication of pSVΔ4, Crandell feline kidney (CrFK) cells (feline adherent cell line) were transfected with 10 μg of either pSV WT or pSVΔ4 and incubated overnight at 37° C. On day 2, transfected CrFK cells were cocultivated with specific pathogen free (SPF) peripheral blood mononuclear cells (PBMC) for approximately 24 hours at 37° C. and then removed from CrFK cell cultures and replated in fresh PBMC media. PBMC cultures were followed for up to 3 weeks for virus production assayed by a FIV p24 antigen capture ELISA on PBMC culture supernatant. In 2 different experiments, virus production from pSVΔ4-infected PBMC was delayed by 4 to 8 days compared to that observed for pSV WT-infected PBMC cultures (FIG. 1). Preliminary characterization of pSVΔ4 indicates that this proviral construct is infectious and that this LTR mutant virus exhibits delayed or slower replication kinetics in feline PBMC compared to pSV-pPPR WT (pSV WT) and exhibits similar replication kinetics to that observed for LTR mutants pSVΔ ATF and pSVΔ AP-1/ATF.

All publications and patent applications mentioned in this Specification are herein incorporated by reference to the same extent as if each of them had been individually indicated to be incorporated by reference.

Although the foregoing invention has been described in some detail by way of illustration and example for purposes of clarity and understanding, it will be obvious that various modifications and changes which are within the skill of those skilled in the art are considered to fall within the scope of the appended claims. Future technological advancements which allow for obvious changes in the basic invention herein are also within the claims.

---

What is claimed is:

1. A non-naturally occurring FIV, wherein the non-naturally occurring FIV is derived from a pathogenic FIV by specifically deleting or mutagenizing one or more of its genes or genetic elements responsible for pathogenicity, and further wherein the non-naturally occurring FIV is attenuated in pathogenicity and elicits an immune response against a pathogenic FIV in a host inoculated with the non-naturally occurring FIV.

2. The non-naturally occurring FIV of claim 1, wherein the genes or genetic element responsible for pathogenicity are selected from the group consisting of: vif, rev, OrfA/2, LTR elements, env, pol, and gag.

3. The non-naturally occurring FIV of claim 2, wherein the non-naturally occurring FIV is selected from the group consisting of:
  (a) a recombinant FIV with a deletion in its vif gene from about a Sau1 restriction site to about a Hind3 restriction site;
  (b) a recombinant FIV with about 4 to 5 nucleotides deleted from the AP-1 and/or ATF sites in the 3' and 5' LTR;
  (c) a recombinant FIV with a deletion in its vif gene from about a Sau1 restriction site to about a Hind3 restriction site, and with about 4 to 5 nucleotides deleted from the AP-1 and/or ATF sites in the 3' and 5' LTR;
  (d) a recombinant FIV with its vif gene, AP-1 and/or ATF sites in the 3' and 5' LTR deleted; and
  (e) a recombinant FIV with about 201 nucleotides removed from the 5' LTR and 4 or 5 nucleotides deleted from the AP-1 and/or ATF sites in the 3' LTR.

4. The non-naturally occurring FIV of claim 3, wherein the recombinant FIV is driven by an SV40pr/RU5 hybrid promoter.

5. The non-naturally occurring FIV of claim 1, wherein the FIV is selected from the group consisting of: FIV-pPPRΔAP-1, FIV-pPPRΔATF, FIV-pPPRΔAP-1/ATF, FIV pSV-pPPRΔATF, FIV pSV-pPPRΔAP-1/ATF, FIV pPPR-pSVΔvif, and FIV-pPPRΔ4.

6. A non-naturally occurring FIV vector with one or more of its genes or genetic elements responsible for pathogenicity being specifically made either absent or fully or partially non-functional, said FIV vector being attenuated in pathogenicity; and said FIV vector preventing or delaying infection of a host by, or limiting dissemination and establishment of, a pathogenic FIV in a host inoculated with the non-naturally occurring FIV.

7. The vector of claim 6, wherein said vector is selected from the group consisting of proviral DNA, genomic RNA, and cDNA.

8. The vector of claim 7, wherein the vector is a live infectious provirus DNA.

9. The vector of claim 8, wherein the genes or genetic elements responsible for pathogenicity are selected from the group consisting of: vif, rev, OrfA/2, LTR elements, env, pol and gag.

10. The vector of claim 9, wherein the vector is a proviral DNA derived from:
  (a) a recombinant FIV with a deletion in its vif gene from about a Sau1 restriction site to about a Hind3 restriction site;
  (b) a recombinant FIV with about 4 to 5 nucleotides deleted from the AP-1 and/or ATF sites in the 3' and 5' LTR;
  (c) a recombinant FIV with a deletion in its vif gene from about a Sau1 restriction site to about a Hind3 restriction site, and with about 4 to 5 nucleotides deleted from the AP-1 and/or ATF sites in the 3' and 5' LTR; and
  (d) a recombinant FIV with its vif gene, AP-1 and/or ATF sites in the 3' and 5' LTR deleted.

11. The vector of claim 7, wherein the vector is selected from the group consisting of pPPRΔvif, pPPRΔAP-1, pPPRΔATF, pPPRΔAP-1/ATF, and pPPRΔ4.

12. A vaccine composition comprising the non-naturally occurring FIV of any of claims 1–4 or 5 in a pharmaceutically acceptable carrier, wherein the non-naturally occurring FIV is live and infectious.

13. A vaccine composition comprising the non-naturally occurring vector of any of claims 6–11, in a pharmaceutically acceptable carrier, wherein the vector is live and infectious.

14. A method for immunizing or treating an animal against infection by an FIV or its related pathogen, comprising the steps of administering to such an animal an attenuated live infectious FIV of any of claims 1–4 or 5.

15. A method for immunizing or treating an animal against infection by an FIV or its related pathogen, comprising the steps of administering the live infectious vector of any of claims 6–11 to such an animal.

16. A vector derived from the non-naturally occurring FIV of claim 1.

17. The vector of claim 16, wherein the non-naturally occurring FIV is selected from the group consisting of: FIV-pPPRΔAP-1, FIV-pPPRΔATF, FIV-pPPRΔAP-1/ATF, FIV pSV-pPPRΔATF, FIV pSV-pPPRΔAP-1/ATF, FIV pPPR-pSVΔvif, and FIV-pPPRΔ4.

18. An FIV provirus construct driven by a SV40pr/RU5 promoter.

19. An FIV virus driven by an SV40pr/RU5 promoter.

20. A method for immunizing or treating a host against FIV infection, said method consisting essentially of administering a single dose of a non-naturally occurring attenuated FIV or a non-naturally occurring FIV vector, wherein protective immunity is achieved as a result of the single dose.

21. A method for treating cats infected with FIV, said method comprising administering to said cats a non-naturally occurring attenuated FIV or a non-naturally occurring FIV vector.

22. A vaccine composition comprising a self-replicating proviral DNA construct including substantially the entire genome of an animal lentivirus with at least one mutation or deletion specifically made within a region responsible for transcription, initiation, or multiplication.

23. A vaccine composition as in claim 22, wherein the DNA construct comprises a circular DNA plasmid with a prokaryotic origin of replication.

24. A vaccine as in claim 23, wherein the deletion is in the LTR.

25. A vaccine as in claim 24, wherein the deletion is in a region selected from the group consisting of: AP1, AP4, ATF, NF-κB, C/EBP, and LBP1.

26. A method for immunizing or treating a host, comprising administering a vaccine composition of any of claims 22–25 to the host.

27. The vector of claim 8, wherein the recombinant FIV is driven by an SV40pr/RU5 hybrid promoter.

28. The non-naturally occurring FIV of claim 2 wherein the non-naturally occurring FIV is selected from the group consisting of:
   (a) a recombinant FIV with about 100 to 600 bases deleted or modified in its vif gene;
   (b) a recombinant FIV with about 30 to 300 bases deleted or modified in its rev gene;
   (c) a recombinant FIV with about 30 to 300 bases deleted or modified in its OrfA/2 gene;
   (d) a recombinant FIV with up to about 20 bases deleted from its NF-κB site;
   (e) a recombinant FIV with up to about 20 bases deleted from its AP-1 site;
   (e) a recombinant FIV with up to about 20 bases deleted from its AP-4 site; and,
   (f) a recombinant FIV with up to about 20 bases deleted from its ATF site.

29. The non-naturally occurring FIV of claim 2 wherein the non-naturally occurring FIV is a recombinant FIV with up to about 20 bases deleted from a site selected from the following group: NF-κB, AP-1, AP-4, and ATF.

30. The non-naturally occurring FIV of claim 29 wherein the non-naturally occurring FIV is a recombinant FIV with up to about 20 bases deleted from two or more sites selected from the following group: NF-κB, AP-1, AP-4, and ATF.

31. A non-naturally occurring FIV vector with one or more of its genes or genetic elements responsible for pathogenicity being specifically made either absent or fully or partially non-functional, said FIV vector being attenuated in pathogenicity.

32. The vector of claim 31, wherein said vector is selected from the group consisting of proviral DNA, genomic RNA, and cDNA.

33. The vector of claim 32, wherein the vector is a live infectious provirus DNA.

34. The vector of claim 31, wherein the gene or genetic element responsible for pathogenicity is selected from the group consisting of: vif, rev, OrfA/2, LTR elements, env, pol, and gag.

35. The vector of claim 34, wherein the gene or genetic element being made fully or partially non-functional is selected from the group consisting of:
   (a) a vif gene with about 100 to 600 bases deleted or modified;
   (b) a rev gene with about 30 to 300 bases deleted or modified;
   (c) an Orf/A gene with about 30 to 300 bases deleted or modified;
   (d) a NF-κB site with up to about 20 bases deleted;
   (e) an AP-1 site with up to about 20 bases deleted;
   (e) an AP-4 site with up to about 20 bases deleted; and,
   (f) an ATF site with up to about 20 bases deleted.

36. The vector of claim 34, wherein the vector has up to about 20 bases deleted from two or more sites selected from the following group: NF-κB, AP-1, AP-4, and ATF.

37. The vector of claim 34, wherein the vector is a DNA derived from:
   (a) a recombinant FIV with a deletion in its vif gene from about a Sau1 restriction site to about a Hind3 restriction site;
   (b) a recombinant FIV with about 4 to 5 nucleotides deleted from the AP-1 and/or ATF sites in the 3' and 5' LTR;
   (c) a recombinant FIV with a deletion in its vif gene from about a Sau1 restriction site to about a Hind3 restriction site, and with about 4 to 5 nucleotides deleted from the AP-1 and/or ATF sites in the 3' and 5' LTR; and
   (d) a recombinant FIV with its vif gene, and AP-1 and/or ATF sites in the 3' and 5' LTR deleted.

38. The vector of claim 32, wherein the vector is selected from the group consisting of pPPRΔvif, pPPRΔAP-1, pPPRΔATF, pPPRΔAP-1/ATF, and pPPRΔ4.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM:  Feline Immunodeficiency Virus-pPPR provirus (xi) SEQUENCE DESCRIPTION: SEQ ID NO:1:

GCGTTGGGAG CTCTCCCATA TGAATCC                                27

(2) INFORMATION FOR SEQ ID NO:2:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: Feline Immunodeficiency Virus-pPPR provirus (xi) SEQUENCE DESCRIPTION: SEQ ID NO:2:

CTGCTAGCGC TTTAACTATG TGTTCAGCTG TTTCCATTTA TCATTTGTTT        50

GTGACAG                                                      57

(2) INFORMATION FOR SEQ ID NO:3:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Feline Immunodeficiency Virus-pPPR provirus (xi) SEQUENCE DESCRIPTION: SEQ ID NO:3:

GATAAATGGA AACAGCTGAA CACATAGTTA AAGCGCTAGC AGCTGCTTAA        50

CCG                                                          53

(2) INFORMATION FOR SEQ ID NO:4:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: Feline Immunodeficiency Virus-pPPR provirus and
            pGEM5Zf(+)

(xi) SEQUENCE DESCRIPTION: SEQ ID NO:4:

GTCGGTCGAC TGCGAAGTTC TCGGCCCGGA TTCCGAGACC                              40

(2) INFORMATION FOR SEQ ID NO:5:

(i) SEQUENCE CHARACTERISTICS:
        (A) LENGTH: 54 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (iv) ANTI-SENSE: YES (vi) ORIGINAL SOURCE:
        (A) ORGANISM: Feline Immunodeficiency Virus-pPPR provirus (xi) SEQUENCE DESCRIPTION: SEQ ID NO:5:

CTTACAGTGG AGCAAATTAT CATTGGCAAG CTTTACATAG GATGTGGTTT                  50

TGCG                                                                    54

(2) INFORMATION FOR SEQ ID NO:6:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Feline Immunodeficiency Virus-pPPR provirus (xi) SEQUENCE DESCRIPTION: SEQ ID NO:6:

CCTATGTAAA GCTTGCCAAG TATAATTTGC TCCACTGTAA GAG                         43

(2) INFORMATION FOR SEQ ID NO:7:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: Feline Immunodeficiency Virus-pPPR provirus (xi) SEQUENCE DESCRIPTION: SEQ ID NO:7:

CTGTCGGGCG CCAACTGCGA AGTTCTCGGC CCGGATTCCG AG                    42

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Feline Immunodeficiency Virus-pPPR provirus (xi) SEQUENCE DESCRIPTION: SEQ ID NO:8:

GGACTAGTTG GGATGAGTAT TGGGACCCTG                                  30

(2) INFORMATION FOR SEQ ID NO:9:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: SV40 genome-early enhancer and promoter (xi) SEQUENCE DESCRIPTION: SEQ ID NO:9:

GACGAGAGCT CACTAGTCCA GCTGTGGAAT GTGTGTCAGT TAGGG                 45

(2) INFORMATION FOR SEQ ID NO:10:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: SV40 genome-early enhancer and promoter (xi) SEQUENCE DESCRIPTION: SEQ ID NO:10:

CGCAGAGATC TGCATAAATA AAAAAAATTA GTCAGCCATG GGGCGGAG              48

(2) INFORMATION FOR SEQ ID NO:11:

(i) SEQUENCE CHARACTERISTICS:
        (A) LENGTH: 49 base pairs
        (B) TYPE: nucleic acid (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Feline Immunodeficiency Virus-34 TF10 provirus (xi) SEQUENCE DESCRIPTION: SEQ ID NO:11:

CGAGGATCCA GATCTTTGTG AAACTTCGAG GAGTCTCTTT GTTGAGGAC                49

(2) INFORMATION FOR SEQ ID NO:12:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (vi) ORIGINAL SOURCE:
            (A) ORGANISM: Feline Immunodeficiency Virus-pPPR provirus (xi) SEQUENCE DESCRIPTION: SEQ ID NO:12:

CAGTCGCTGC AGCGGGCGCC AACTGCGAAG TTCTCGGC                            38

(2) INFORMATION FOR SEQ ID NO:13:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (vi) ORIGINAL SOURCE:
            (A) ORGANISM: Feline Immunodeficiency Virus-pPPR provirus (xi) SEQUENCE DESCRIPTION: SEQ ID NO:13:

GTCGGGCGCG CCATAATTTG CTCCACTGTA AG                                  32

(2) INFORMATION FOR SEQ ID NO:14:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (vi) ORIGINAL SOURCE:
    (A) ORGANISM: Feline Immunodeficiency Virus-pPPR provirus (xi) SEQUENCE DESCRIPTION: SEQ ID NO:14:

GTCGGTCGAC GGCGCGCCTG TTCAGCTGTT TCCATTTATC        40